(12) United States Patent
Finch et al.

(10) Patent No.: US 10,405,780 B2
(45) Date of Patent: Sep. 10, 2019

(54) LOWER LIMB LOADING ASSESSMENT SYSTEMS AND METHODS

(71) Applicant: IMEASUREU Limited, Parnell (NZ)

(72) Inventors: Mark Finch, St. Mary's Bay (NZ); Thor Franciscus Besier, Devonport (NZ)

(73) Assignee: IMEASUREU Limited, Parnell (NZ)

( * ) Notice: Subject to any disclaimer, the term of this patent is extended or adjusted under 35 U.S.C. 154(b) by 166 days.

(21) Appl. No.: 15/128,808

(22) PCT Filed: Feb. 18, 2015

(86) PCT No.: PCT/IB2015/051206
§ 371 (c)(1),
(2) Date: Sep. 23, 2016

(87) PCT Pub. No.: WO2015/145273
PCT Pub. Date: Oct. 1, 2015

(65) Prior Publication Data
US 2018/0020950 A1    Jan. 25, 2018

(30) Foreign Application Priority Data

Mar. 25, 2014  (NZ) ........................................ 622954

(51) Int. Cl.
*A61B 5/00*    (2006.01)
*A61B 5/11*    (2006.01)
(Continued)

(52) U.S. Cl.
CPC ............ *A61B 5/112* (2013.01); *A61B 5/1036* (2013.01); *A61B 5/1124* (2013.01);
(Continued)

(58) Field of Classification Search
None
See application file for complete search history.

(56) References Cited

U.S. PATENT DOCUMENTS 5,485,402 A    1/1996 Smith et al.
8,968,218 B2 *  3/2015 Wukasch ............ A61B 5/1038
600/587
(Continued)

FOREIGN PATENT DOCUMENTS

NZ           329288 A    8/2001
WO    WO-2013190835 A2    12/2013
(Continued)

OTHER PUBLICATIONS

"Installation and Operating Manual: Model 356A32, Platinum Stock Products; Triaxial, mini (5 gm) high sensitivity, ICP accel.", Manual No. 18292; PCB Piezotronics, Vibration Division, Depew, New York, Copyright 2002, (2002), 17 pgs.
(Continued)

*Primary Examiner* — Max F Hindenburg
(74) *Attorney, Agent, or Firm* — Schwegman Lundberg & Woessner, P.A.

(57) ABSTRACT

A lower loading assessment system having at least one motion sensor mounted to a subject's lower limb that is configured to sense the tibial shockwaves experienced by the lower limb as the subject performs a repetitive physical activity involving repetitive footstrikes of the lower limb with a surface. The motion sensor comprises an accelerometer that is configured to sense acceleration data in at least three axes and generate representative acceleration data over a time period associated with the physical activity. The acceleration data represents a series of discrete tibial shockwaves from the discrete footstrikes. A data processor receives the tibial shockwave data and processes that to generate output feedback data comprising data to assist the subject to minimize future loading in their lower limbs.

48 Claims, 17 Drawing Sheets

(51) Int. Cl.
*A61B 5/103* (2006.01)
*G01P 15/00* (2006.01)
*G01P 15/18* (2013.01)

(52) U.S. Cl.
CPC .... *A61B 5/6829* (2013.01); *A61B 2562/0219* (2013.01); *G01P 15/00* (2013.01); *G01P 15/18* (2013.01)

(56) References Cited

U.S. PATENT DOCUMENTS

| | | | |
|---|---|---|---|
| 8,988,240 B2* | 3/2015 | Burton | A63B 24/0062 |
| | | | 340/686.1 |
| 9,446,287 B2* | 9/2016 | Weast | A61B 5/112 |
| 9,999,378 B2* | 6/2018 | Ronchi | A61B 5/4595 |
| 2006/0236748 A1 | 10/2006 | Nose et al. | |
| 2011/0270135 A1 | 11/2011 | Dooley et al. | |
| 2012/0119904 A1 | 5/2012 | Coleman et al. | |
| 2013/0085700 A1 | 4/2013 | Modi et al. | |

FOREIGN PATENT DOCUMENTS

| | | |
|---|---|---|
| WO | WO-2014022877 A1 | 2/2014 |
| WO | WO-2015/145273 A1 | 10/2015 |

OTHER PUBLICATIONS

"International Application No. PCT/IB2015/051206, International Preliminary Report on Patentability dated Mar. 29, 2016", 5 pgs.

"International Application No. PCT/IB2015/051206, International Search Report dated May 5, 2015", (May 5, 2015), 4 pgs.

"International Application No. PCT/IB2015/051206, Response filed Feb. 26, 2016 to Written Opinion dated May 5, 2015", 34 pgs.

"International Application No. PCT/ B2015/051206, Written Opinion dated May 5, 2015", 6 pgs.

Barnes, Andrew, "Field based gait retraining to reduce lower extremity loads in runners", [online]. [retrieved on Sep. 19, 2016]. Retrieved from the Internet: <URL: http:www.shu.ac.uk/research/cser/case-studies/field-based-gait-retraining-reduce-lower-extremity-loads-runners>, (2014), 1 pg.

Crowell, Harrison P., et al., "Gait Retraining to Reduce Lower Extremity Loading in Runners", Published in final edited form as: *Clin Biomech* (Bristol, Avon), 26(1), 78-83 (2011), 78-83, (2011), 17 pgs.

Crowell, Harrison P., et al., "Reducing Impact Loading During Running With the Use Journal of Real-Time Visual Feedback", *Journal of Orthopedic & Sports Physical Therapy*, 40(4), (Apr. 2010), 206-213.

Sinclair, J., et al., "Gender Differences in the Kinetics and Kinematics of Distance Running: Implications for Footwear Design", *International Journal of Sports Science and Engineering*, vol. 6, No. 2, (2012), 118-128.

Taha, Zahari, et al., "An Overview of Sports Engineering: History, Impact and Research", *Movement, Healthy & Exercise*, vol. 2, (2013), 1-14.

"New Zealand Application No. 706172, First Examination Report dated Apr. 3, 2017", (Apr. 3, 2017), 5 pgs.

"New Zealand Application No. 706172, Further Examination Report dated Nov. 30, 2017", (Nov. 30, 2017), 3 pgs.

"New Zealand Application No. 706172, Further Examination Report dated Mar. 9, 2018", (Mar. 9, 2018), 4 pgs.

"New Zealand Application No. 706172, Response to Examination Report dated Nov. 2, 2017", (Nov. 2, 2017), 123 pgs.

"New Zealand Application No. 706172, Response to Examination Report dated Feb. 26, 2018", (Feb. 26, 2018), 3 pgs.

Barnes, Andrew, et al., "Field based gait retraining to reduce lower extremity loads in runners", Uploaded Jan. 14, 2019 [https://www.shu.ac.uk/research/specialisms/centre-for-sports-engineering-research/case-studies/biomechanics/field-based-gait-retraining-to-reduce-lower-extremity-loads-in-runners], (Mar. 19, 2014), 2 pgs.

Clarke, T. E., et al., "Effects of Shoe Cushioning Upon Ground Reaction Forces in Running", Int. J. Sports Med. 4 (1983) 247-251, (1983), 247-251.

Crowell, Harrison Crowell, et al., "Gait Retraining to Reduce Lower Extremity Loading in Runners", Clin Biomech (Bristol, Avon). Jan. 2011; 26(1): 78-83, (Jan. 2011), 78-83.

Lafortune, Mario A., "Three-Dimensional Acceleration of the Tibia During Walking and Running", Journal of Biomechanics vol. 24, Issue 10 pp. 877-879, 881-886 (1991), (1991), 881-886.

Taha, Zahari, et al., "An Overview of Sports Engineering: History, Impact and Research", Movement, Health & Exercise, 2, 1-14 (2013), (2013), 1-14.

* cited by examiner

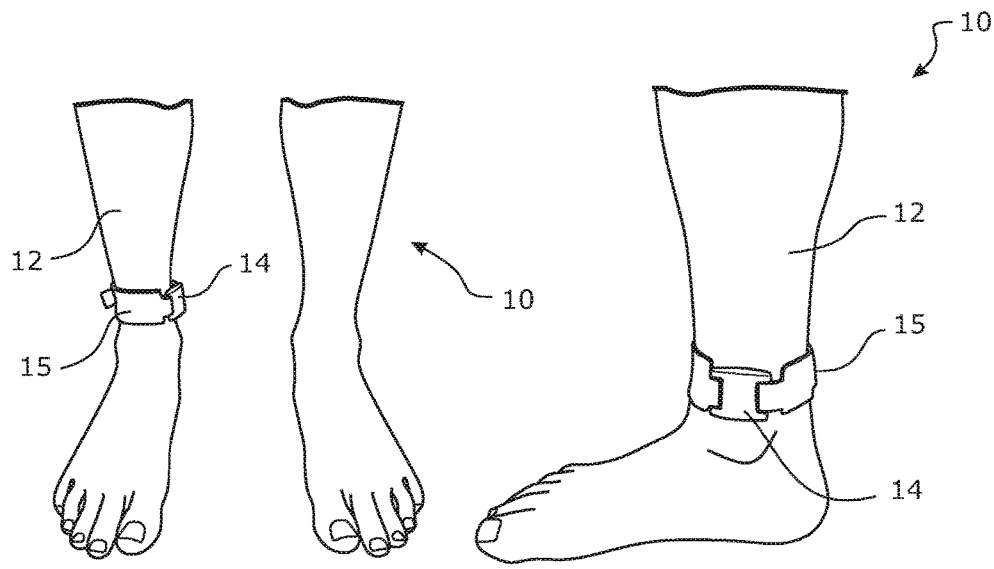
*FIGURE 2A*  *FIGURE 2B*
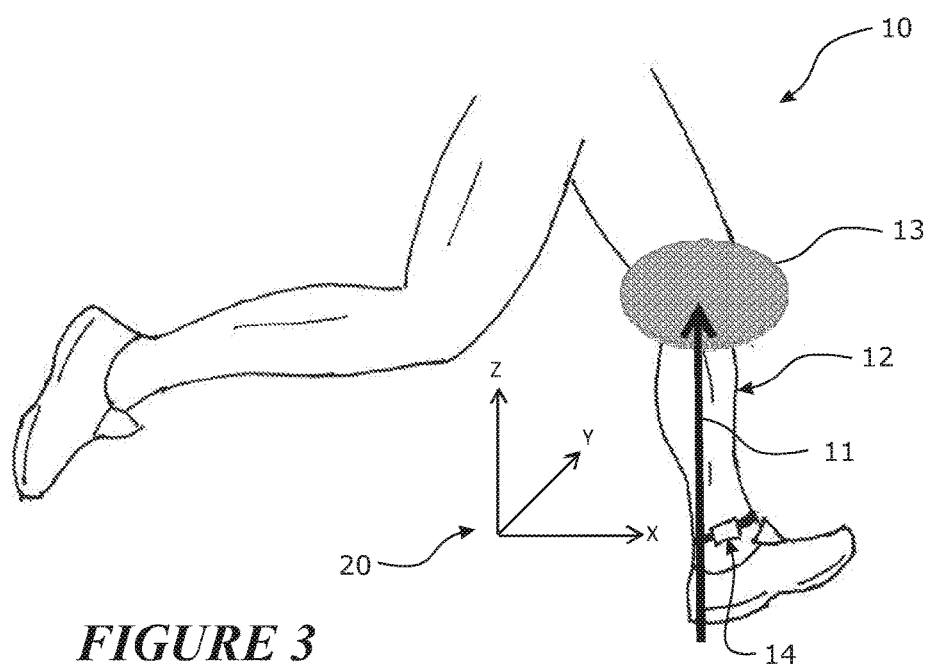
*FIGURE 3*

LOWER LIMB LOADING ASSESSMENT SYSTEMS AND METHODS

PRIORITY CLAIM TO RELATED APPLICATIONS

This application is a U.S. national stage application filed under 35 U.S.C. § 371 from International Application Serial No. PCT/IB2015/051206, which was filed 18 Feb. 2015, and published as WO2015/145273 on 1 Oct. 2015, and which claims priority to New Zealand Application No. 622954, filed 25 Mar. 2014, which applications and publication are incorporated by reference as if reproduced herein and made a part hereof in their entirety, and the benefit of priority of each of which is claimed herein.

FIELD OF THE INVENTION

The present invention relates to lower limb loading assessment systems and methods for activities such as, but not limited to, running.

BACKGROUND TO THE INVENTION

Musculoskeletal tissues, such as bone, muscle, tendon and cartilage, respond and adapt to their local mechanical environment in such a manner as to maintain a stable equilibrium, or homeostasis. Mechanical loads are also responsible for injury to musculoskeletal tissue and are critical for the rehabilitation and regeneration of the tissue. In its broadest sense, injury occurs when the loads experienced by the tissue exceed the strength of that tissue. These loads might be traumatic, such as a direct impact or single loading event causing failure, or cumulative, where repeated loads result in damage.

During running, for example, reaction forces of 2-3 times body weight are transmitted from the ground, through the foot and into the lower limb via the ankle, knee and hip joints. The musculoskeletal tissues, particularly muscle and tendon, attenuate transient impact loads as they travels up the limb. Over the course of a 5 km run, the average runner will strike the ground approximately 3,000 times and this repetitive loading has been associated with common overuse injuries, such as patellofemoral pain, plantar fasciitis, fatigue fractures, and Achilles tendinopathy.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

It is an object of the present invention to provide lower limb loading assessment systems and methods which generate outputs that can be used to minimize lower limb injury, or to at least provide the public with a useful choice.

In a first aspect, the invention broadly consists in a lower limb loading assessment system comprising: at least one motion sensor mounted to a subject's lower limb that is configured to sense the tibial shockwaves experienced by the lower limb as the subject performs a repetitive physical activity involving repetitive footstrikes of the lower limb with a surface, the motion sensor comprising a an accelerometer that is configured to sense acceleration data in at least three axes and generate representative acceleration data over a time period associated with the physical activity, the motion sensor generating tibial shockwave data comprising the generated acceleration data which represents a series of discrete tibial shockwaves from the discrete footstrikes; and a data processor that is configured to receive the tibial shockwave data sensed by the motion sensor, and wherein the data processor is configured to process the received tibial shockwave data to generate output feedback data comprising data to assist the subject to minimize future loading in their lower limbs.

In an embodiment, the data processor is configured to extract or calculate one or more variables from the received tibial shockwave data and compare the or each variable to a predetermined threshold or thresholds, and provide feedback data in the form of a real-time alert signal if one or more of the thresholds is exceeded by its associated variable.

In an embodiment, the data processor is configured to: convert the 3-axes acceleration data of the tibial shockwave data into resultant acceleration magnitude data, and extract peak shock variables representing the peak resultant acceleration magnitude data associated with each discrete footstrike.

In an embodiment, the data processor is configured to generate a real-time alert signal if any peak shock variables exceed a predetermined threshold.

In an embodiment, the data processor is configured to calculate an average peak shock variable representing the average of the extracted peak shock variables, and wherein the data processor is configured to generate a real-time alert signal if the average peak shock variable exceeds a predetermined threshold.

In an embodiment, the data processor is configured to generate footstrike pattern variables representing the footstrike pattern associated with each footstrike as defined by the profile of the resultant acceleration magnitude data for a period associated with each discrete footstrike, and generate a real-time alert signal if any of the footstrike pattern variables exceed a predetermined footstrike pattern threshold.

In an embodiment, the data processor is configured to generate footstrike pattern variables representing the footstrike pattern associated with each footstrike as defined by the profile of the acceleration data in three axes for a period associated with each discrete footstrike, and generate a real-time alert signal if any of the footstrike pattern variables exceed a predetermined footstrike pattern threshold.

In an embodiment, the data processor is configured to generate the footstrike pattern variables based on tibial shockwave data for each discrete footstrike between heelstrike and toe-off time locations.

In an embodiment, the system further comprises one or more feedback devices mounted to or carried by the user that are triggered by in response to a generated real-time alert signal.

In an embodiment, the feedback devices comprise any one or more of the following: tactile feedback devices, audible feedback devices, and/or visual feedback devices.

In an embodiment, the data processor is configured to process the tibial shockwave data to generate feedback data in the form of data indicative of a session load stimulus.

In an embodiment, the data processor is configured to receive tibial shockwave data from a plurality of activity sessions of the subject from a single day, and generate feedback data in the form data indicative of a daily load stimulus.

In an embodiment, the data processor is configured to identify the time locations of the heelstrikes associated with each footstrike, and generate feedback data in the form of cadence representing the average time between heelstrikes.

In an embodiment, the data processor is configured to: receive tibial shockwave data from a plurality of separate activity sessions, convert the 3-axes acceleration data of the tibial shockwave data into resultant acceleration magnitude data, extract peak shock values representing the peak resultant acceleration magnitude associated with each discrete footstrike of the tibial shockwave data of each of the separate activity sessions, calculate the average peak resultant acceleration magnitude for each of the separate activity sessions based on the extracted peak shock values, and generate feedback data representing the calculated average peak resultant acceleration magnitude for each separate activity session.

In an embodiment, the subject is wearing a different type of footwear in each separate activity session, and the data processor is configured to receive or associate unique identification data relating to each different type of footwear used by the subject with the respective tibial shockwave data of each activity session, and the feedback data generated comprises data representing the calculated average peak resultant acceleration magnitude of each separate activity session linked with the unique identification data relating to the footwear used in the activity session.

In an embodiment, the data processor is further configured to compare the calculated average peak resultant acceleration magnitude associated with each activity session and generate further feedback data identifying the activity session having the lowest peak resultant acceleration magnitude.

In an embodiment, the three axes of the 3-axis accelerometer are orthogonal to each other.

In an embodiment, the data processor is communicatively coupled to the motion sensor over a data link. In another embodiment, the preceding claims wherein the data processor is onboard the motion sensor.

In an embodiment, the motion sensor is mounted to the subject's lower limb between the femoral epicondyle and medial malleolus.

In an embodiment, the motion sensor is mounted to the subject's lower limb in the region of the lower $1/3^{rd}$ of the tibia.

In an embodiment, the motion sensor is mounted to the subject's lower limb in the region of the medial part of the tibia.

In an embodiment, the motion sensor is mounted to the subject's lower limb in the region adjacent and above the medial malleolus of the tibia.

In an embodiment, the motion sensor is mounted to the subject's lower limb in the region adjacent and above the lateral malleolus of the tibia.

In a second aspect, the invention broadly consists in a method of assessing the loading on a subject's lower limb at the subject performs a repetitive physical activity involving repetitive footstrikes of the lower limb with a surface, the method implemented on a computing device and comprising: receiving tibial shockwave data comprising sensed acceleration data from at least one motion sensor mounted to the subject's lower limb that comprises an accelerometer that is configured to sense and generate acceleration data in at least three axes, the sensed acceleration data representing a series of discrete tibial shockwaves from the discrete footstrikes; and processing the tibial shockwave data to generate output feedback data comprising data to assist the subject to minimize future loading in their lower limbs.

In an embodiment, the method comprises extracting or calculating one or more variables from the received tibial shockwave data, comparing the or each variable to a predetermined threshold or thresholds, and generating feedback data in the form of a real-time alert signal if one or more of the thresholds is exceeded by its associated variable.

In an embodiment, the method comprises converting the 3-axes acceleration data of the tibial shockwave data into resultant acceleration magnitude data, and extracting peak shock variables representing the peak resultant acceleration magnitude data associated with each discrete footstrike.

In an embodiment, the method further comprises generating a real-time alert signal if any peak shock variables exceed a predetermined threshold.

In an embodiment, the method further comprises calculating an average peak shock variable representing the average of the extracted peak shock variables, and generating a real-time alert signal if the average peak shock variable exceeds a predetermined threshold.

In an embodiment, the method further comprises generating footstrike pattern variables representing the footstrike pattern associated with each footstrike as defined by the profile of the resultant acceleration magnitude data for a period associated with each discrete footstrike, and generating a real-time alert signal if any of the footstrike pattern variables exceed a predetermined footstrike pattern threshold.

In an embodiment, the method further comprises generating footstrike pattern variables representing the footstrike pattern associated with each footstrike as defined by the profile of the acceleration data in three axes for a period associated with each discrete footstrike, and generating a real-time alert signal if any of the footstrike pattern variables exceed a predetermined footstrike pattern threshold.

In an embodiment, the method comprises generating the footstrike pattern variables by based on tibial shockwave data for each discrete footstrike between heelstrike and toe-off time locations.

In an embodiment, the method comprises triggering one or more feedback devices mounted to or carried by the user in response to a generated real-time alert signal.

In an embodiment, the feedback devices comprise any one or more of the following: tactile feedback devices, audible feedback devices, and/or visual feedback devices.

In an embodiment, the method comprises processing the tibial shockwave data to generate feedback data in the form of data indicative of a session load stimulus.

In an embodiment, the method comprises receiving tibial shockwave data from a plurality of activity sessions of the subject from a single day, and generating feedback data in the form data indicative of a daily load stimulus.

In an embodiment, the method comprises identifying the time locations of the heelstrikes associated with each footstrike, and generating feedback data in the form of cadence representing the average time between heelstrikes.

In an embodiment, the method comprises receiving the tibial shockwave data from a plurality of separate activity sessions, converting the 3-axes acceleration data of the tibial shockwave data into resultant acceleration magnitude data, extracting peak shock values representing the peak resultant acceleration magnitude associated with each discrete footstrike of the tibial shockwave data of each of the separate activity sessions, calculating the average peak resultant acceleration magnitude for each of the separate activity sessions based on the extracted peak shock values, and generating feedback data representing the calculated average peak resultant acceleration magnitude for each separate activity session.

In an embodiment, the subject is wearing a different type of footwear in each separate activity session, and the data processor is configured to receive or associate unique identification data relating to each different type of footwear used by the subject with the respective tibial shockwave data of each activity session, and the feedback data generated comprises data representing the calculated average peak resultant acceleration magnitude of each separate activity session linked with the unique identification data relating to the footwear used in the activity session.

In an embodiment, the method comprises comparing the calculated average peak resultant acceleration magnitude associated with each activity session and generating further feedback data identifying the activity session having the lowest peak resultant acceleration magnitude.

In an embodiment, the three axes of the 3-axis accelerometer are orthogonal to each other.

In an embodiment, the motion sensor is mounted to the subject's lower limb between the femoral epicondyle and medial malleolus.

In an embodiment, the motion sensor is mounted to the subject's lower limb in the region of the lower $\frac{1}{3}^{rd}$ of the tibia.

In an embodiment, the motion sensor is mounted to the subject's lower limb in the region of the medial part of the tibia.

In an embodiment, the method comprises the motion sensor is mounted to the subject's lower limb in the region adjacent and above the medial malleolus of the tibia.

In an embodiment, the method comprises the motion sensor is mounted to the subject's lower limb in the region adjacent and above the lateral malleolus of the tibia.

In a third aspect, the invention broadly consists in a lower limb loading assessment system comprising:

at least one motion sensor mounted to a subject's lower limb that is configured to sense the tibial shockwaves experienced by the lower limb as the subject performs a repetitive physical activity involving repetitive footstrikes of the lower limb with a surface, the motion sensor generating tibial shockwave data representing a series of discrete tibial shockwaves from the discrete footstrikes; and a data processor that is configured to receive the tibial shockwave data sensed by the motion sensor, and wherein the data processor is configured to process the received tibial shockwave data to generate output feedback data comprising data to assist the subject to minimize future loading in their lower limbs.

In an embodiment, the motion sensor comprises an accelerometer that is configured to sense acceleration data in at least three axes and generate representative acceleration data over a time period associated with the physical activity, the tibial shockwave data comprising the acceleration data.

In a fourth aspect the invention broadly consists in a computer-readable medium having stored thereon computer executable instructions that, when executed on a processing device, cause the processing device to perform the method of the second aspect of the invention.

The third and fourth aspects of the invention may have any one or more of the features mentioned in respect of the first and second aspects of the invention.

Other configurations are also described below.

Also described is a first configuration comprising a lower limb shock assessment system comprising: one or more motion sensors mounted to a subject's lower limb which are configured to sense the tibial shockwaves experienced by the lower limb as the subject performs a repetitive physical activity and which generate representative tibial shockwave data; and a computing device that is configured to receive the tibial shockwave data sensed by the one or more sensors from a plurality of separate activity sessions, the subject performing the same repetitive physical activity in each activity session, and wherein the processor is configured to generate assessment data based on the tibial shockwave data from the activity sessions.

In one embodiment, the sensor(s) are configured to transmit the tibial shockwave data to the computing device over a wireless communication medium. In another embodiment, the sensor(s) are configured to transmit the tibial shockwave data to the computing device over a hardwired communication medium.

In one form, the sensor(s) may comprise a transmitter module for transmitting the data to the computing device either directly, or via an intermediate receiver module operatively connected to the computing device.

In an embodiment, the system comprises a single motion sensor mounted to the subject's lower limb. The motion sensor may comprise a 3-axis accelerometer. The 3-axis accelerometer may be configured to measure raw acceleration data with respect to three separate axes. In one form, the three axes are orthogonal to each other. In this form, the raw three-axes acceleration data corresponds to the tibial shockwave data.

In one form, the motion sensor is configured to generate resultant acceleration magnitude data based on the raw three-axis acceleration data, and this resultant acceleration magnitude data represents the tibial shockwave data. In another form, the computing device receives the raw three-axis acceleration data from the motion sensor and generates the resultant acceleration magnitude data representing the tibial shockwave data.

In one embodiment, the repetitive physical activity is running or walking on a surface. In this embodiment, the tibial shockwave data comprises data representing a series of discrete tibial shockwaves, each tibial shockwave corresponding to a discrete foot strike when the subject's foot strikes the surface. In one form, the tibial shockwave data for each activity session is sensed for a predetermined time period. Typically, the predetermined time period is identical for each activity session.

In one embodiment, the computing device is configured to: determine the peak resultant acceleration magnitude for each discrete tibial shockwave in the series of the activity session; and calculate the average peak resultant acceleration magnitude over the series. In one form, the computing device is configured to generate a tibial shock score for each activity session based on or corresponding to the determined average peak resultant acceleration magnitude of the series of discrete tibial shockwaves in the activity session. In one embodiment, the tibial shock score may be the average peak resultant acceleration magnitude or the magnitude converted into a normalized value within a predetermined tibial shock score scale.

In one example, the subject may be wearing a different type (e.g. style, model, size) of footwear for each activity session. In one configuration, the computing device may be configured to receive or associate unique identification data relating to each different type of footwear used by the subject with the respective tibial shockwave data of each activity session, and is further configured to generate assessment data associating the tibial shock score of each activity session with the footwear used in the activity session. In another configuration, the computing device may be configured to generate assessment data representing the tibial shock score for each activity session.

In one configuration, the computing device may be configured to generate assessment data based on a comparison of the tibial shock scores from each activity session. In one example, the computing device may be configured to generate assessment data which identifies the activity session having the lowest tibial shock score, which corresponds to the lowest overall tibial shock experienced by the subject's lower limb during the activity session. In a further example, if each activity session is linked to a unique identification data relating to the footwear used in the activity session, the computing device may be configured to output assessment data relating to the footwear having the lowest tibial shock score for the subject.

In one form, the computing device comprises a display for displaying the tibial shockwave data and/or assessment data. The data may be displayed numerically, table-form, graphically, or a combination of these.

In one form, the subject may be a human and the assessment system may be employed for assessing and comparing the tibial shock experienced by the human when running in different types of footwear.

Also described is a second configuration comprising a method of assessing lower limb shock of a subject over a plurality of activity sessions, comprising: receiving tibial shockwave data from one or more motion sensors mounted to the subject's lower limb which are configured to sense the tibial shockwaves experienced by the lower limb as the subject performs a repetitive physical activity and which generate representative tibial shockwave data; processing the received tibial shockwave data from a plurality of separate activity sessions, the subject performing the same repetitive physical activity in each activity session; and generating assessment data based on the tibial shockwave data from the activity sessions.

In one embodiment, the method comprises receiving the tibial shockwave data from the motion sensor(s) over a wireless communication medium. In another embodiment, the method comprises receiving the tibial shockwave data from the motion sensor(s) over a hardwired communication medium.

In one embodiment, the method comprises receiving the tibial shockwave data from a transmitter module(s) of the motion sensor(s), either directly or via an intermediate receiver module in data communication with the transmitter module(s).

In an embodiment, the method comprises receiving the tibial shockwave data from a single motion sensor mounted to the subject's lower limb. The motion sensor may comprise a 3-axis accelerometer. The 3-axis accelerometer may be configured to measure raw acceleration data with respect to three separate axes. In one form, the three axes are orthogonal to each other. In this form, the raw three-axes acceleration data corresponds to the tibial shockwave data.

In one form, the motion sensor is configured to generate resultant acceleration magnitude data based on the raw three-axis acceleration data, and the method comprises receiving this resultant acceleration magnitude data representing the tibial shockwave data from the motion sensor. In another form, the method comprises receiving the raw three-axis acceleration data from the motion sensor and calculating the resultant acceleration magnitude data representing the tibial shockwave data.

In one embodiment, the repetitive physical activity is running or walking on a surface. In this embodiment, the tibial shockwave data comprises data representing a series of discrete tibial shockwaves for the activity session, each tibial shockwave corresponding to a discrete foot strike when the subject's foot strikes the surface. In one form, the method comprises receiving tibial shockwave data sensed over a predetermined time period for each activity session. Typically, the predetermined time period is identical for each activity session.

In one embodiment, the method further comprises determining the peak resultant acceleration magnitude for each discrete tibial shockwave in the series of the activity session; and calculating the average peak resultant acceleration magnitude over the series. In one form, the method further comprises generating a tibial shock score for each activity session based on or corresponding to the determined average peak resultant acceleration magnitude of the series of discrete tibial shockwaves in the activity session. In one embodiment, the tibial shock score may be the average peak resultant acceleration magnitude or the magnitude converted into a normalized value within a predetermined tibial shock score scale.

In one example, the subject may be wearing a different type (e.g. style, model, size) of footwear for each activity session. In one embodiment, the method may further comprise: receiving or associating unique identification data relating to each different type of footwear used by the subject with the respective tibial shockwave data of each activity session; and generating assessment data associating the tibial shock score of each activity session with the footwear used in the activity session. In another embodiment, the method may further comprise generating assessment data representing the tibial shock score for each activity session.

In one embodiment, the method may further comprise generating assessment data based on a comparison of the tibial shock scores from each activity session. In one example, the method may comprise generating assessment data which identifies the activity session having the lowest tibial shock score, which corresponds to the lowest overall tibial shock experienced by the subject's lower limb during the activity session. In a further example, if each activity session is linked to a unique identification data relating to the footwear used in the activity session, the method may comprise generating assessment data relating to the footwear having the lowest tibial shock score for the subject.

In one form, the method may further comprise displaying the tibial shockwave data and/or assessment data on a display screen. The data may be displayed numerically, table-form, graphically, or a combination of these.

In one form, the subject may be a human and the assessment system may be employed for assessing and comparing the tibial shock experienced by the human when running in different types of footwear.

Also described is a third configuration comprising a lower limb shock assessment system comprising: one or more motion sensors mounted to a subject's lower limb which are configured to sense the tibial shockwaves experienced by the lower limb as the subject performs physical activity and which generate representative tibial shockwave data; and a computing device that is configured to receive the tibial shockwave data sensed by the one or more sensors, and wherein the processor is configured to process the received data and generate an estimate of the subject's daily load stimulus (DLS).

In one embodiment, the computing device is configured to compare the generated DLS to a threshold DLS stored for the subject, and generate an alert or notification if the threshold is exceeded.

Also described is a fourth configuration comprising a method of assessing lower limb shock of a subject, comprising: receiving tibial shockwave data from one or more motion sensors mounted to the subject's lower limb which are configured to sense the tibial shockwaves experienced by the lower limb as the subject performs a physical activity and which generate representative tibial shockwave data; processing the received tibial shockwave data; and generating an estimate of the subject's daily load stimulus (DLS).

In one embodiment, the method further comprises comparing the generated DLS to a threshold DLS stored for the subject, and generating an alert or notification if the threshold is exceeded.

The third and fourth configurations may have any one or more of the features mentioned in respect of the first and second configurations of the invention.

Also described is a fifth configuration comprising a lower limb shock assessment system comprising: one or more motion sensors mounted to a subject's lower limb which are configured to sense the tibial shockwaves experienced by the lower limb as the subject performs physical activity and which generate representative tibial shockwave data; and a computing device that is configured to receive the tibial shockwave data sensed by the one or more sensors, and wherein the processor is configured to process the received data to analyse the subject's gait, and generate output data indicative of modifications to the subject's gait that will reduce tibial shock.

Also described is a sixth configuration comprising a method of assessing lower limb shock of a subject, comprising: receiving tibial shockwave data from one or more motion sensors mounted to the subject's lower limb which are configured to sense the tibial shockwaves experienced by the lower limb as the subject performs a physical activity and which generate representative tibial shockwave data; processing the received tibial shockwave data to analyse the subject's gait; and generating output data indicative of medications to the subject's gait that will reduce tibial shock.

The fifth and sixth configurations may have any one or more of the features mentioned in respect of the first-fourth configurations.

Also described is a seventh configuration comprising a computer-readable medium having stored thereon computer executable instructions that, when executed on a processing device, cause the processing device to perform any of the methods or associated features of the second, fourth, and sixth configurations.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

Number Ranges

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term "and/or" means "and" or "or", or both.

As used herein "(s)" following a noun means the plural and/or singular forms of the noun.

The invention consists in the foregoing and also envisages constructions of which the following gives examples only.

BRIEF DESCRIPTION OF THE DRAWINGS

Preferred embodiments of the invention will be described by way of example only and with reference to the drawings, in which:

FIGS. 2A and 2B are front and side elevation view of a user wearing a motion sensor of the lower limb loading assessment system on their lower leg;

FIG. 3 is a schematic diagram showing the sensor axes of the motion sensor with respect to the user's lower leg;

DETAILED DESCRIPTION OF PREFERRED EMBODIMENTS

Figure 1:
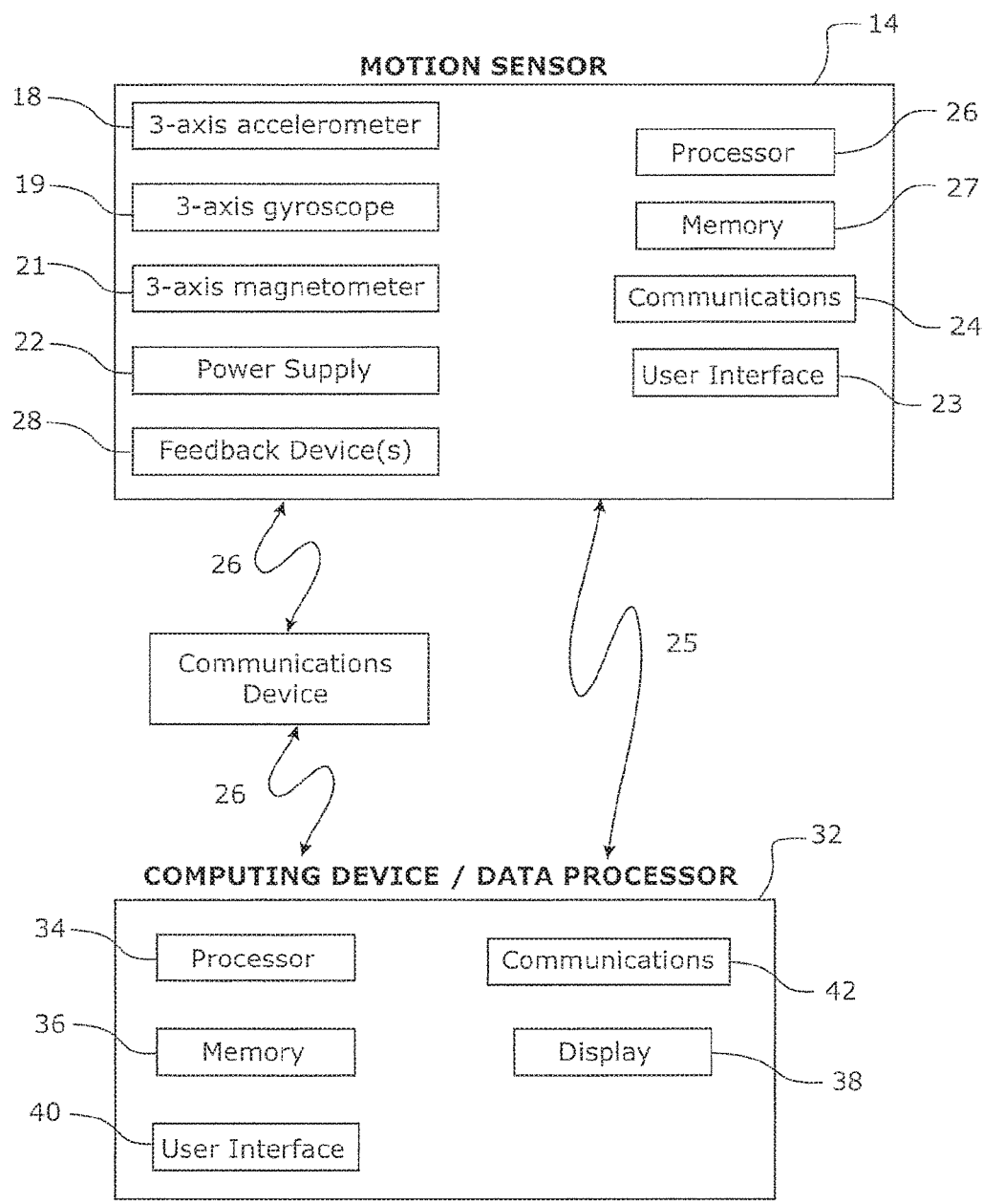
FIG. 1 is a schematic diagram of the hardware components of the lower limb loading assessment system in accordance with an embodiment of the invention.

In the following description, specific details are given to provide a thorough understanding of the embodiments. However, it will be understood by one of ordinary skill in the art that the embodiments may be practiced without these specific details. For example, software modules, functions, circuits, etc., may be shown in block diagrams in order not to obscure the embodiments in unnecessary detail. In other instances, well-known modules, structures and techniques may not be shown in detail in order not to obscure the embodiments.

Also, it is noted that the embodiments may be described as a process that is depicted as a flowchart, a flow diagram, a structure diagram, or a block diagram. Although a flowchart may describe the operations as a sequential process, many of the operations can be performed in parallel or concurrently. In addition, the order of the operations may be rearranged. A process is terminated when its operations are completed. A process may correspond to a method, a function, a procedure, a subroutine, a subprogram, etc., in a computer program. When a process corresponds to a function, its termination corresponds to a return of the function to the calling function or a main function.

Aspects of the systems and methods described below may be operable on any type of general purpose computer system, computing device, or other programmable device, including, but not limited to, a desktop, laptop, notebook, tablet or mobile device. The term "mobile device" includes, but is not limited to, a wireless device, a mobile phone, a smart phone, a wearable electronic device such as a smart watch or head-mounted display device, a mobile communication device, a user communication device, personal digital assistant, mobile hand-held computer, a laptop computer, an electronic book reader and reading devices capable of reading electronic contents and/or other types of mobile devices typically carried by individuals and/or having some form of communication capabilities (e.g., wireless, infrared, short-range radio, etc.).

1. Overview

The lower limb loading assessment system and methods relate to measuring and monitoring the mechanical loads experienced by musculoskeletal tissue associated with the lower limb, and this is critical to reducing risk of injury as well as prescribing appropriate training strategies to recover from injury. The high frequency transient loads that travel up the limb are referred to in this description as 'tibial shockwaves'. The lower limb loading assessment system senses, analyses and monitors these tibial shockwaves to generate or output various feedback metrics and/or data in the context of various different applications of the lower limb loading assessment system. In general terms, the lower limb loading assessment system employs body-worn sensors and a subject-specific biomechanical model to estimate tissue loading. The system employs a mechanobiological framework to provide the user with actionable feedback metrics to do any one or more of the following: monitor and adjust running technique, analyse training sessions, or assess longer-term tissue health. These actionable feedback metrics have application to reduce risk of injury and/or provide meaningful metrics to modify a user's running technique or training regime.

Various embodiments of the systems and methods of the lower limb loading assessment system will be described. In a first embodiment, a real-time running gait feedback system will be described which provides a runner with real-time feedback on how loads were being transferred into their lower limbs, and enables them to make adjustments to their running technique to reduce tissue loads for a given running speed based on that feedback. In a second embodiment, a cumulative loading monitoring system will be described that is capable of monitoring tibial shockwaves throughout an exercise or activity session, e.g. a run on a particular route, to identify regions of the run that corresponded to high loads, which might be due to terrain and grade, muscle fatigue, or changes in running technique, and feedback that information to the user. Obtaining a cumulative measurement of load could also indicate to the runner if their musculoskeletal tissue is at risk of fatigue damage, or whether they have received enough load to maintain tissue health over a longer time frame. In a third embodiment, a shoe-fitting feedback system will be described.

It will be appreciated that the various embodiments of the lower limb loading assessment system to be described may be employed independently or may be combined in various forms. The embodiments of the system employ similar hardware components and aspects of data processing, some of which will first be described below.

Hardware

Referring to FIGS. 1-3, runners 10 exhibit unique style/technique, and it has been identified that runners will exhibit a unique form of tibial shockwave 11 that travels up their lower extremity 12 as they run. Each runner 10 can be considered as having their own 'shock signature'. The lower limb loading assessment system is configured to sense and record a person's shock signature as they run using a motion sensor or sensors 14, such as accelerometers attached to person's lower limb segment(s) of interest.

Tibial shock is a metric for loading at the knee 13, which can be quantified using accelerometry. Using the knowledge of the subject's mass, Newton's second law (F=ma) can be applied to find the total force transmitted through the leg 12.

The most common type of running injury is located in the knee, therefore tibial shock is a good surrogate measure of impact force at the knee, which is relatable to the risk of injury. Shin splints (tibial stress reactions or tibial fatigue fractures) are also common examples of overuse running injuries and have been associated with increased tibial shock.

Referring to FIG. 1, in the various embodiments of the lower limb loading assessment system, the subject person 10 is provided with one or more wearable and portable motion sensors on 14 on each or one of their lower limbs that sense movement as the user runs. The motion sensor 14 may be secured to the subject's lower limb 12 by a releasable strap 15, which may be elastic or non-elastic. In some embodiments, the strap 15 may comprise a fastening system to tighten the strap around the limb such as, but not limited to, a buckle, hook and loop fastening system or similar, although this is not essential in the case of some elastic straps.

In this embodiment, the motion sensor 14 is positioned or attached to the medial part of the tibia. Typically the sensor 14 is positioned between the femoral epicondyle and medial malleolus. The sensor 14 is typically attached tightly to the limb so as to measure the movement and/or shockwave associated with the underlying bone, rather than the movement of the skin and soft tissue. In one configuration, the sensor 14 is located in the region of the distal $\frac{1}{3}^{rd}$ of the tibia as this does not impinge on the triceps surae muscle group. Additionally, this region is ideal for proving haptic or tactile feedback to the user, in the context of the real-time running gait feedback system embodiment. In another configuration, the sensor is positioned just above the lateral malleolus of the fibula on the subject's ankle.

In this embodiment, the motion sensor 14 is an inertial measurement unit (IMU) and comprises a housing within which an accelerometer sensor 18 is mounted. The accelerometer is configured to measure acceleration with respect to at least one sensor-axes, but preferably two or multiple-axes. In this embodiment, the motion sensor is provided with a 3-axis accelerometer 18 that is configured to sense and measure accelerations along three separate sensor-axes. In this embodiment, the three sensor-axes are orthogonal to each other as shown by the X, Y, Z-axes 20 in FIG. 3. For example, the Z-axis is configured to measure accelerations in a direction extending along the subjects tibia, the X-axis is configured to measure accelerations in a fore-aft direction transverse to the Z-axis, and the Y-axis is configured to measure accelerations in a side-side direction transverse to the Z-axis.

In this embodiment, the motion sensor additionally comprises a 3-axis gyroscope sensor 19 configured to sense angular velocity, and generate representative angular velocity signals, and a 3-axis magnetometer sensor 21 configured to sense the earth's magnetic field and generate representative magnetic field signals. In this embodiment, the sensor 14 is configured to operate the 3-axis accelerometer, gyroscope, and magnetometer sensors 18,19,21 concurrently or simultaneously to sense and generate their respective 3-axis sensor signals. In one configuration, the gyroscope and magnetometer sensors are 3-axis sensors, and are aligned or calibrated to have sensor-axes that are co-aligned with each other and the 3-axis accelerometer 18. In an alternative configuration, the sensors 18, 19, 21 may sense raw signals along different sensor-axes, but the sensor signals/data generated may be processed and transformed into a common 3-axis co-ordinate or sensor-axes system. It will be appreciated that the motion sensor need not comprise the gyroscope and/or magnetometer sensors in alternative embodiments.

In this embodiment, the motion sensor 14 further comprises a user interface 23, such as an on/off switch, buttons, display or touch-screen display, to enable the unit to be operated and/or controlled. A power supply or source 22, such as a battery, rechargeable or otherwise, is provided to power the circuitry and electronic components of the motion sensor 14. A wireless data communication module 24 is provided that is configured to communicate over a wireless data link 25 with a computing device 32, to receive control signals or transmit the sensed sensor data to the computing device 32. The motion sensor 14 also comprises a controller 26, such as a processor or microcontroller or microprocessor for controlling the components of the motion sensor, along with associated memory 27 for storing, temporarily or permanently, sensed data from the 3-axis sensors, for processing and/or transmission to the computing device 32. One or more operable feedback devices 28 are also provided to provide tactile, audio and/or visual feedback to the wearer, such as vibration devices, auditory devices and/or display or lights.

In this embodiment, the communications module comprises a wireless transmitter/receiver that uses a wireless transmission medium or link 25, such as Bluetooth, infrared, RF, WiFi, NFC or the like. Alternatively, a hardwired cable connection to the computing device may be used for the data transmission in other embodiments.

In this embodiment, the motion sensor 14 may be configured to communicate directly 25 with the computing device 32 or indirectly 26 via an intermediate communications relay device that is operatively connected, wirelessly or hardwired, to the computing device 32. In one example, the communications relay device may be the wearer's smart phone, smart watch, or another wearable or mobile computing device. In either configuration, sensed data may be transmitted continuously or in batches. It will be appreciated that the sensor signals may be digitally sampled at the desired sampling frequency or otherwise generate digital sensor signals.

The computing device 32 may be a general purpose computer, such as a desktop, laptop, notebook, or any other form of portable or non-portable computing device, including tablet, PDA, smart phone, smart watch, head-mounted display, wearable computer or similar. The computing device 32 typically comprises a processor 34, memory 36, display 38, a user interface 40, such as a keyboard, mouse, touch-screen or similar, and a communications module 42 for communicating with the motion sensor 14, either directly 25 or indirectly 26. Alternatively, the computing device 32 may be a stand-alone processing system. In other configurations, the computing device may be in the form of a remote data processing system or data processing server. For example, the motion sensor 14 may transmit the sensed data, directly or indirectly, to a cloud-based data processing system.

Data Processing

Depending on the application of the lower limb loading assessment system, the data processing of the sensed data may be carried out in different configurations. In some configurations, the motion sensor 14 itself carries out all data processing and generates all the required feedback information or metrics for the user, without any exterior data processing. In other configurations, the motion sensor 14 may perform no or minimal data processing, and may send the raw sensed data continuously or periodically to the computing device 32 for data processing to generate the feedback information or metrics. It will be appreciated that the data processing may be carried out in real-time for some applications, and at the end of the activity session or a range of activity sessions in other applications.

Figure 4A:
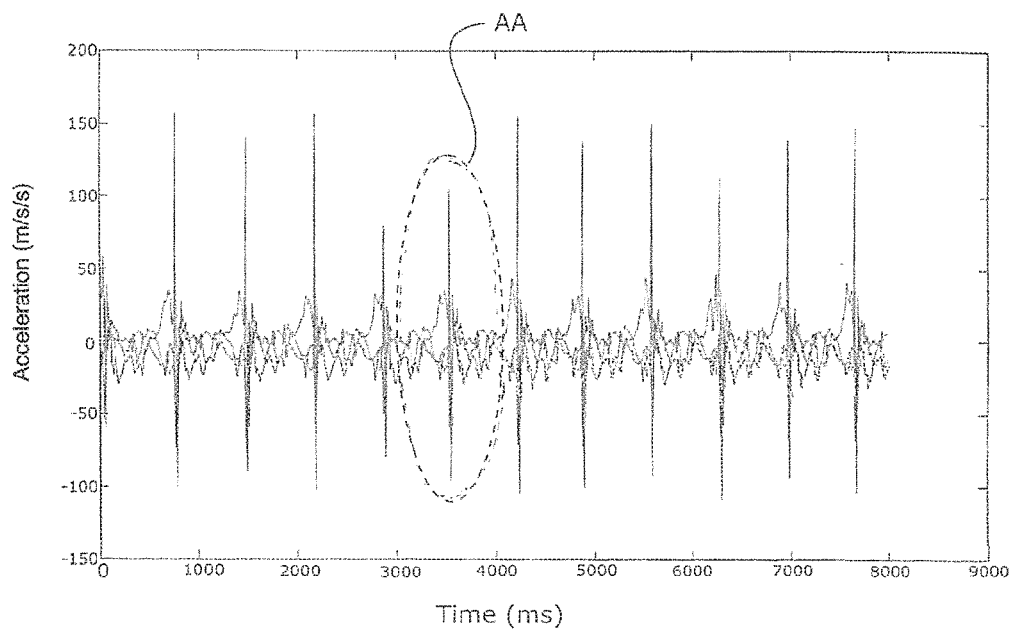
FIG. 4A is a graph depicting measured raw 3-axis acceleration data plotted against time sensed by the motion sensor of the lower limb loading assessment system for a series of foot-strikes recorded while the user was running.
Figure 4B:
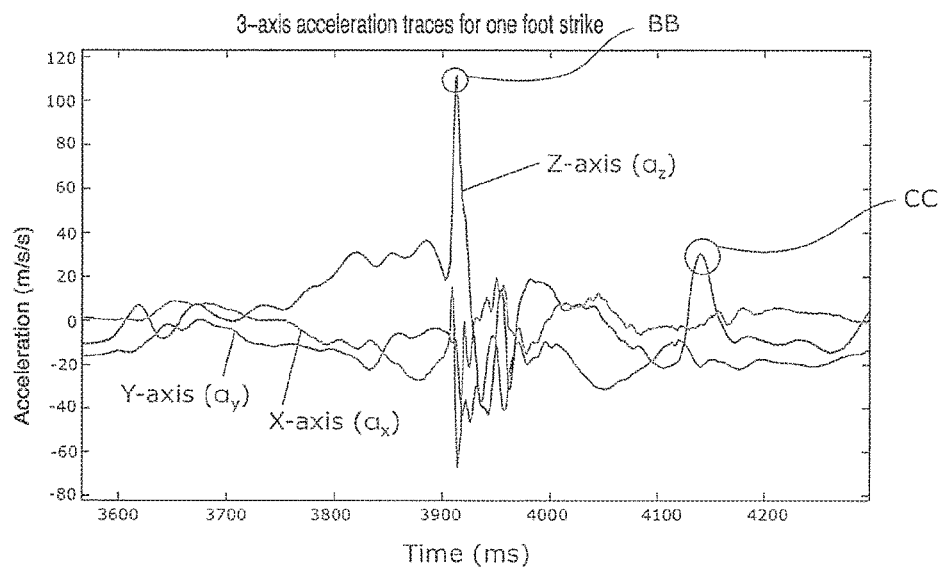
FIG. 4B is a graph depicting the measured raw 3-axis acceleration data against time for 3 separate sensor axes as sensed by the motion sensor for the single discrete foot-strike indicated at AA in FIG. 4A.

During an assessment session, the user's tibial shockwave data representing the tibial shockwaves experienced during footstrikes with surface is derived from the 3-axis acceleration data sensed by the 3-axis accelerometer 18 in the motion sensor 14. By way of example with reference to FIG. 4A, a portion of measured raw 3-axis acceleration data for an activity session is shown. A series of discrete foot-strikes is visible. FIG. 4B shows a close-up of the foot-strike identified as AA in FIG. 4A. The close-up shows the acceleration readings sensed for the foot-strike in each of the X, Y and Z-axes previously described. The individual foot-strikes can be analysed to determine the 'heel-strike' BB and 'toe-off' CC regions, e.g. times, of each foot-strike. The time-location of the individual heel-strike and/or toe-off regions can assist in later determining peak acceleration and cadence.

Shock Signatures

Depending on the embodiment, the individuals shock signature may be defined in various ways. In some embodiments, the shock signature is defined by the varying profile of the magnitude of each of the 3-axes of raw acceleration data over a time period, such as for example either for an individual foots-strike (e.g. between 'heel-strike' and 'toe-off') or the data between the start of each foot-strike for example. In other embodiments, the resultant acceleration magnitude of the 3-axes of raw acceleration data is calculated, and the shock signature may be defined as the profile of the varying resultant acceleration magnitude over a time period, such as for example an individual footstrike or between the start of successive footstrikes. All conditions being equal (e.g. terrain, speed, footwear, fatigue level, etc), the individuals shock signature should substantially repeat for successive footstrikes.

Peak Shock

The data processing is configured to receive and process the raw 3-axis acceleration data (shown in FIGS. 4A and 4B), and calculate the resultant acceleration magnitude data at each time sample. The resultant acceleration magnitude (magnitude of the resultant acceleration vector) at each time sample is calculated as:

$$\bar{a} = \sqrt{a_x^2 + a_y^2 + a_z^2} \quad (1)$$

The peak shock for each individual foot-strike may be determined by the magnitude of the resultant acceleration vector at the location of the heelstrike in each footstrike, as this is when the maximum shock occurs in the foot-strike. The peak shock is typically dependent on a number of factors including, but not limited to, the user's shoes, the terrain upon which they are running, their running technique or style, and any orthotics they are using. The individual peak shocks for an activity session may be averaged to generate an average peak shock for that activity session.

Footstrike Pattern

Figure 5:
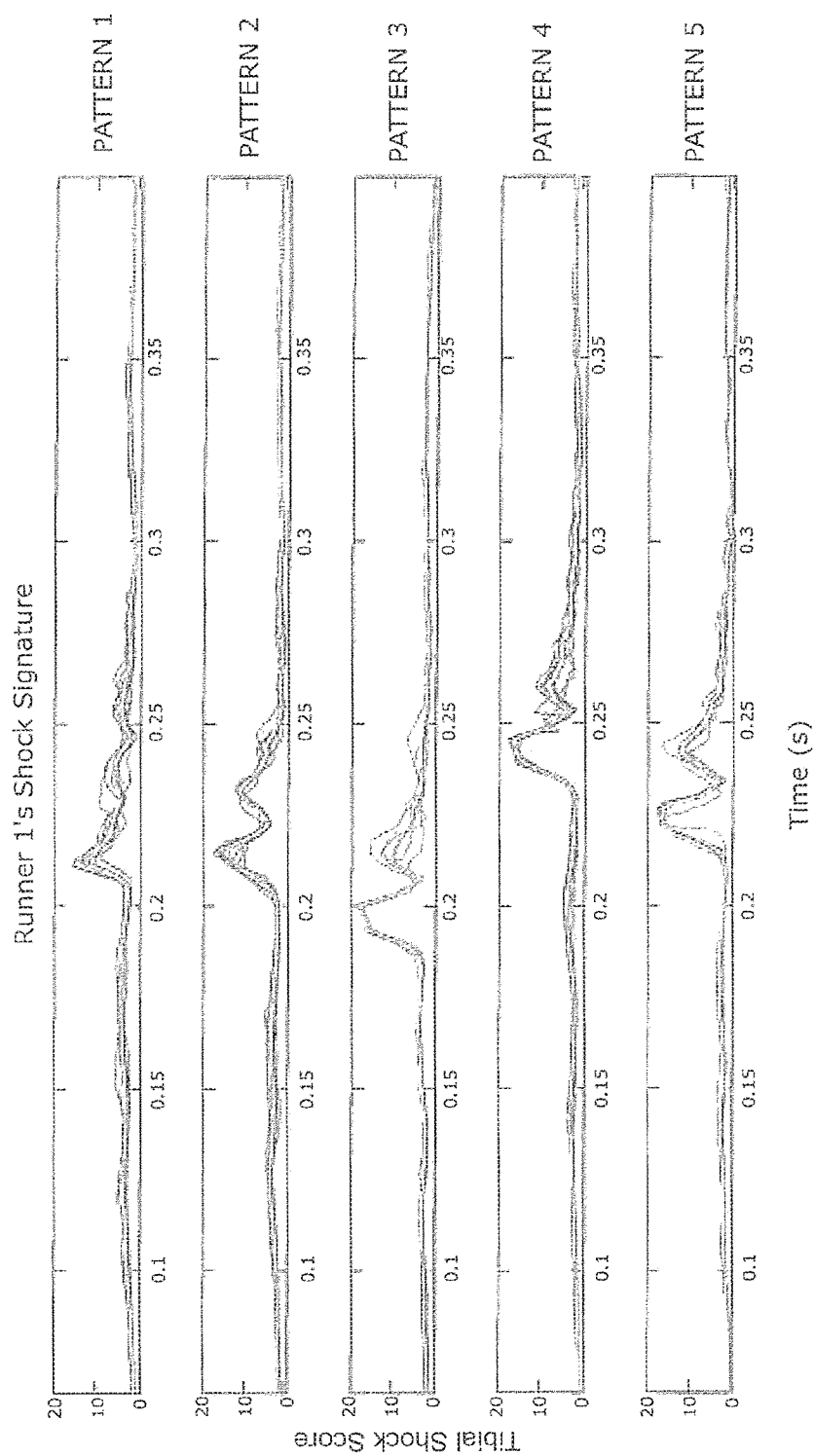
FIG. 5 shows graphs plotting an overlay of normalized resultant acceleration magnitude data against time, the data representing the discrete tibial shockwaves sensed by the motion sensor over 5 separate activity sessions, and showing how a user's footstrike pattern may vary depending on various factors.

An individual's footstrike pattern affects accumulative load, and therefore overuse injuries, through varying footstrike magnitudes resulting from a change in running technique. A runner will change their technique for various reasons including, but not limited to, terrain changes, using different footwear, when fatigue occurs, and in the early stages of an injury settling in. By way of example, FIG. 5 shows various foot-strike patterns of the same runner due to a change in their running style of technique.

Individual runners generate their own unique tibial shock signature when their foot comes in contact with the ground during running. The resultant acceleration magnitude data may be analysed with pattern recognition algorithms to record and store the user's 'normal' footstrike pattern. In one configuration, the footstrike pattern may be defined by the profile of resultant acceleration magnitude between the heelstrike and toe-off positions in a foot-strike. The data processing may analyse whether the user's sensed footstrike pattern during an activity session or part of an activity session deviates beyond a predetermined threshold relative to their 'normal' stored footstrike pattern, and output feedback data representing the time period or periods during the activity session in which the deviations occurred. The reason for the change in footstrike pattern may then be identified by reviewing the factors associated with those time periods in the activity session.

In other configurations, the individual's footstrike patterns for different conditions, e.g. terrain, speed, footwear, or the like may be stored, and pattern recognition algorithms may analyse the tibial shockwave data sensed from an activity session to identify which periods of the activity session match previously stored footstrike patterns, to thereby enable the terrain, speed, footwear or other aspects of the activity session to be determined.

Example of Tibial Shockwave Data Sensed for Different Footwear

Figures 6A, 6B:
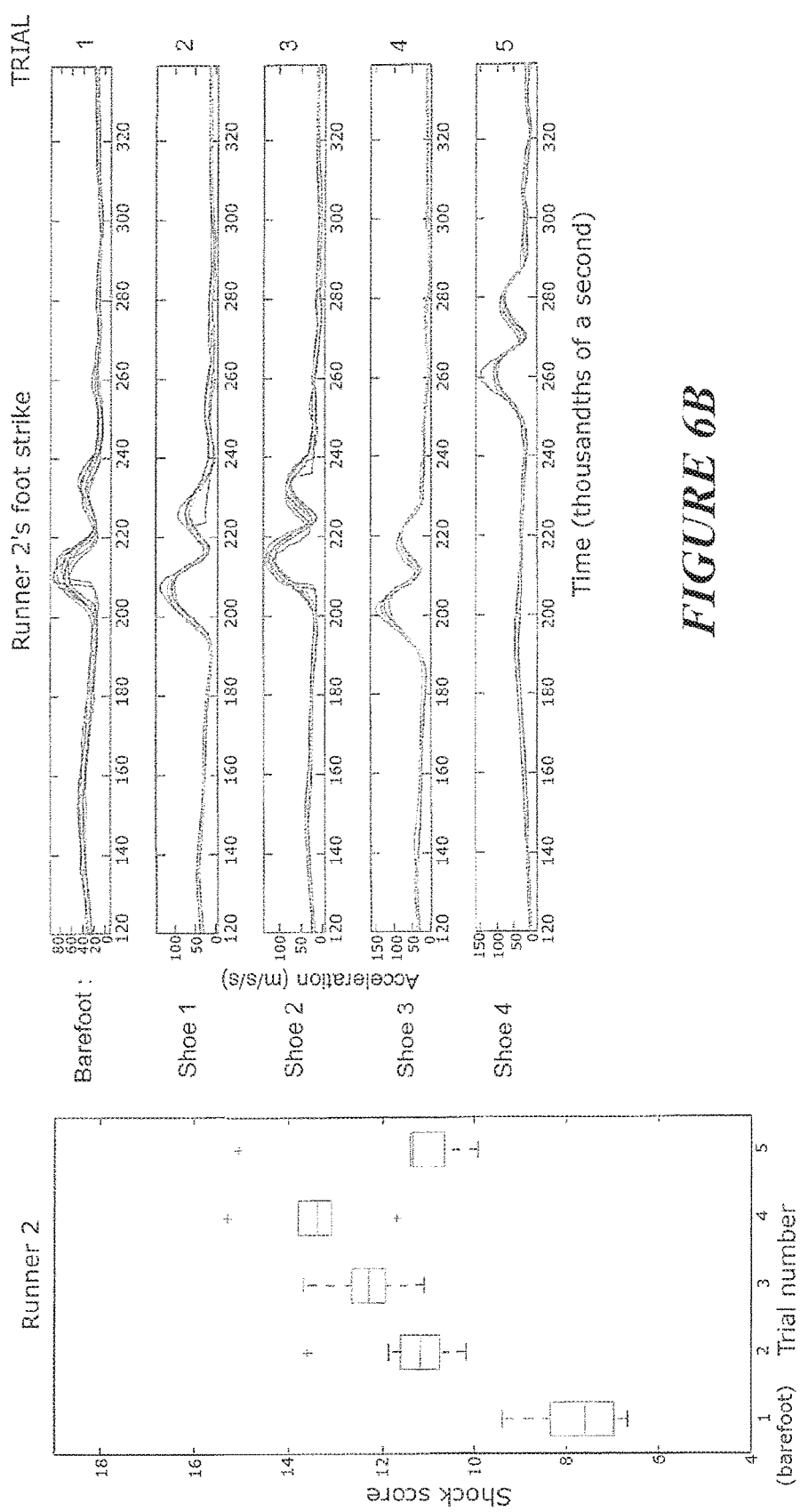
FIGS. 6A and 6B show box-and-whisker plots and graphs plotting an overlay of resultant acceleration magnitude data against time, the data representing the discrete tibial shockwaves sensed by the motion sensor over 5 separate activity sessions in which the user's footwear is different in each session.

By way of example, FIGS. 6A and 6B show the resultant acceleration magnitude data sensed for a number of trials in which the runner wears different footwear, and in one case runs barefoot. The individual footstrikes from each session are shown in overlay in FIG. 6B against time. FIG. 6A shows the box-and-whisker plots of the peak shocks recorded for each activity session. As shown, the type of footwear worn by the runner has an impact on the tibial shockwaves experienced by the user.

Example of Tibial Shockwave Data Sensed Over Different Terrain

By way of example, FIGS. 7A-7D show the resultant acceleration magnitude data sensed for a number of trials in which the runner runs on different terrain. The terrains include road, grass, hard sand, and soft sand. The graphs illustrate the different running shock signatures (e.g. the substantially repeating profile of the resultant acceleration magnitude between the start of each footstrike) and shock magnitudes from running on different terrains. It can be seen that the harder the surface, the greater the shock magnitude, which contributes to a larger accumulative load.

When comparing road to sand, the shock signature (e.g. the profile of the resultant acceleration magnitude as it varies between successive footstrikes) also changes dramatically. The softer the surface, the greater the amount of leg movement (an example of which is circled in each graph). As noted above, this change in shock signature (e.g. footstrike pattern) can be used to identify what kind of running the runner is doing, i.e. what surface they are running on and how there technique changes to adjust for a change in surface.

Figure 7A:
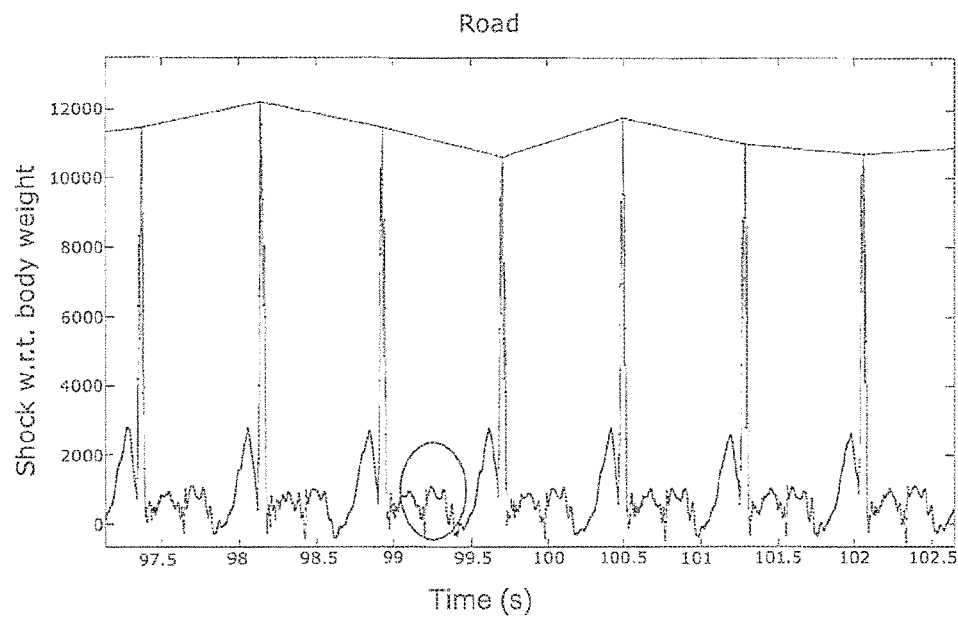
FIGS. 7A-7D show graphs plotting resultant acceleration magnitude data, normalized with respect to body weight, against time, the data representing the series of tibial shockwaves sensed by the motion sensor as the user runs on 4 different terrains, specifically road, grass, hard sand, and soft sand.
Figure 7B:
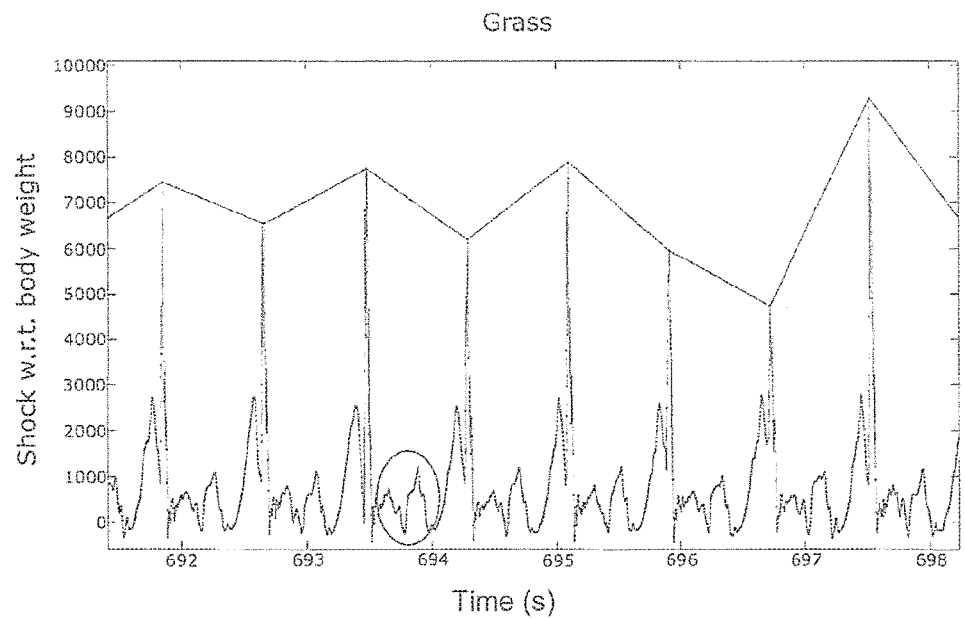
Figure 7C:
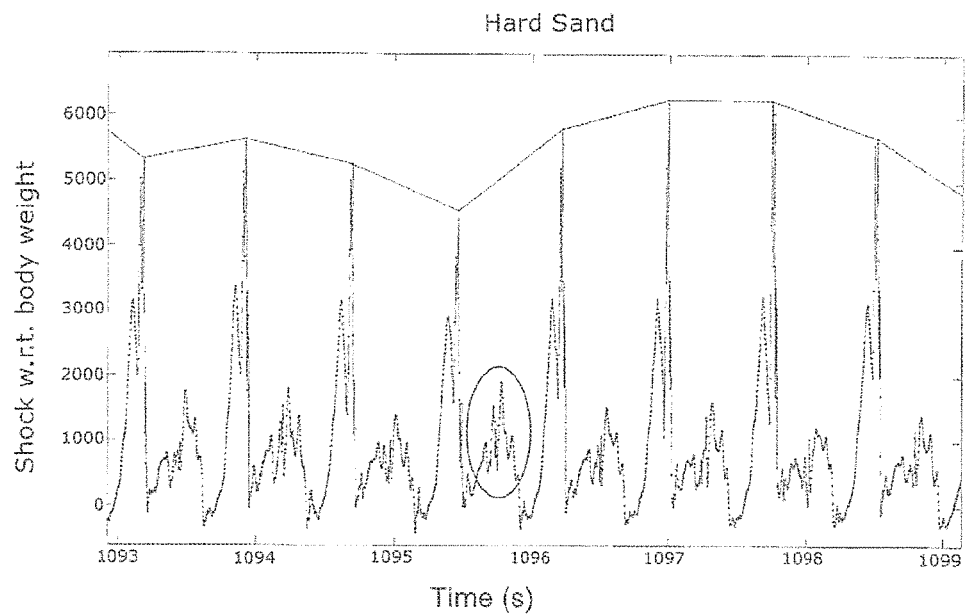
Figure 7D:
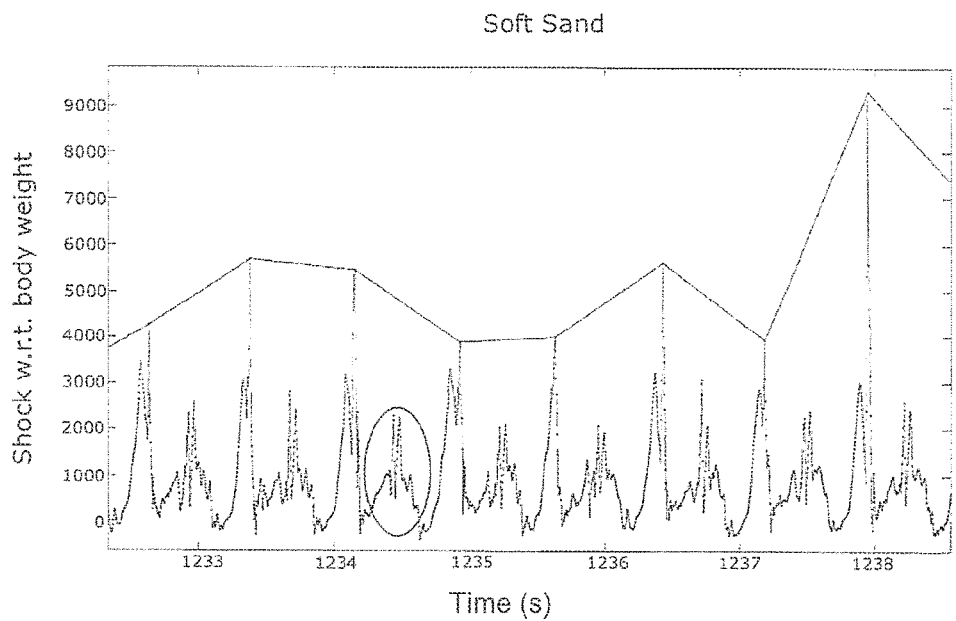
Figure 7E:
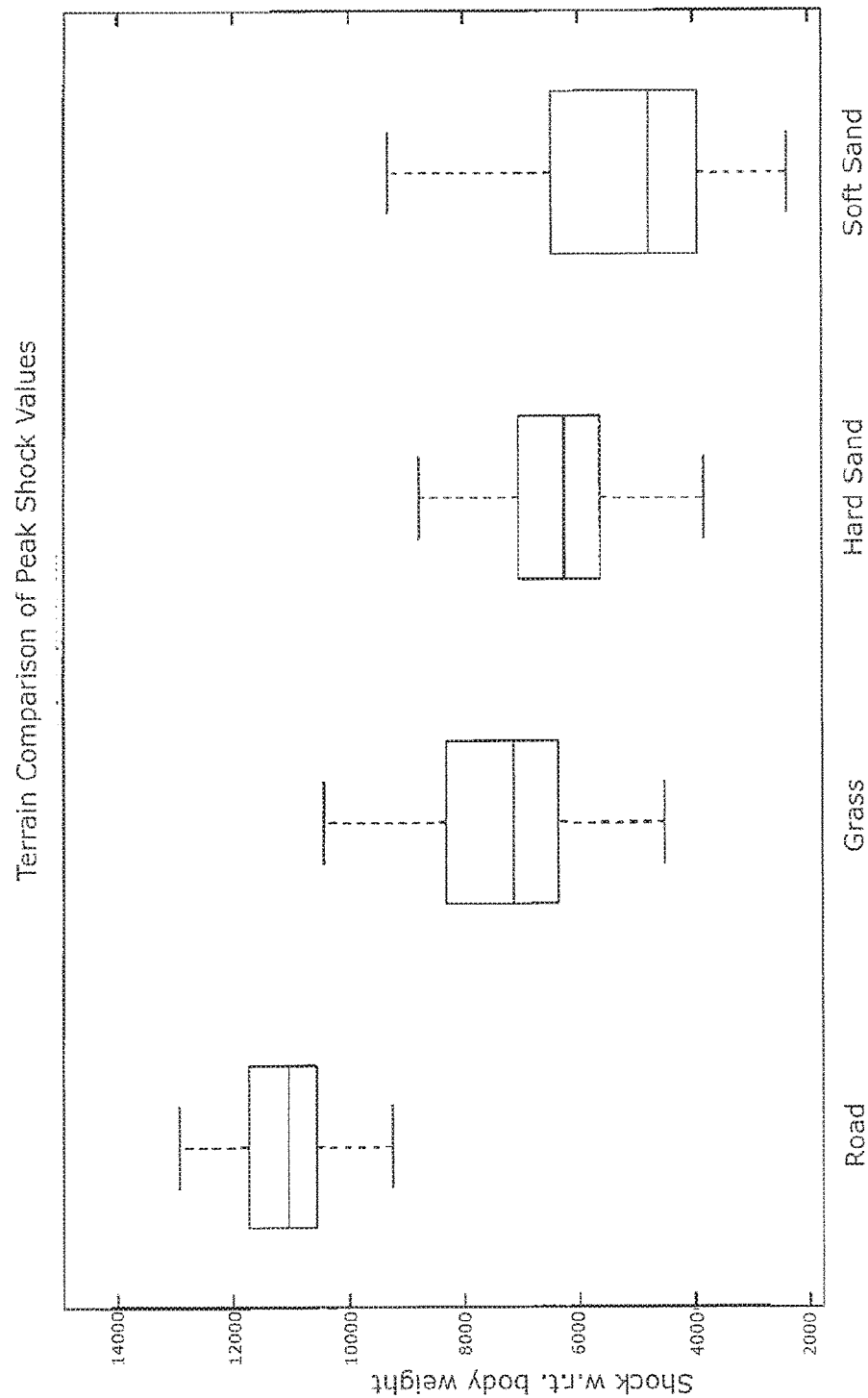
FIG. 7E shows box-and-whisker plots of the peak resultant acceleration magnitude data, normalized with respect to body weight, of FIGS. 7A-7D for the 4 different terrains.

FIG. 7E shows the box-and-whisker plot of the peak shocks recorded for each terrain, from the data in FIGS. 7A-7D.

Figure 7F:
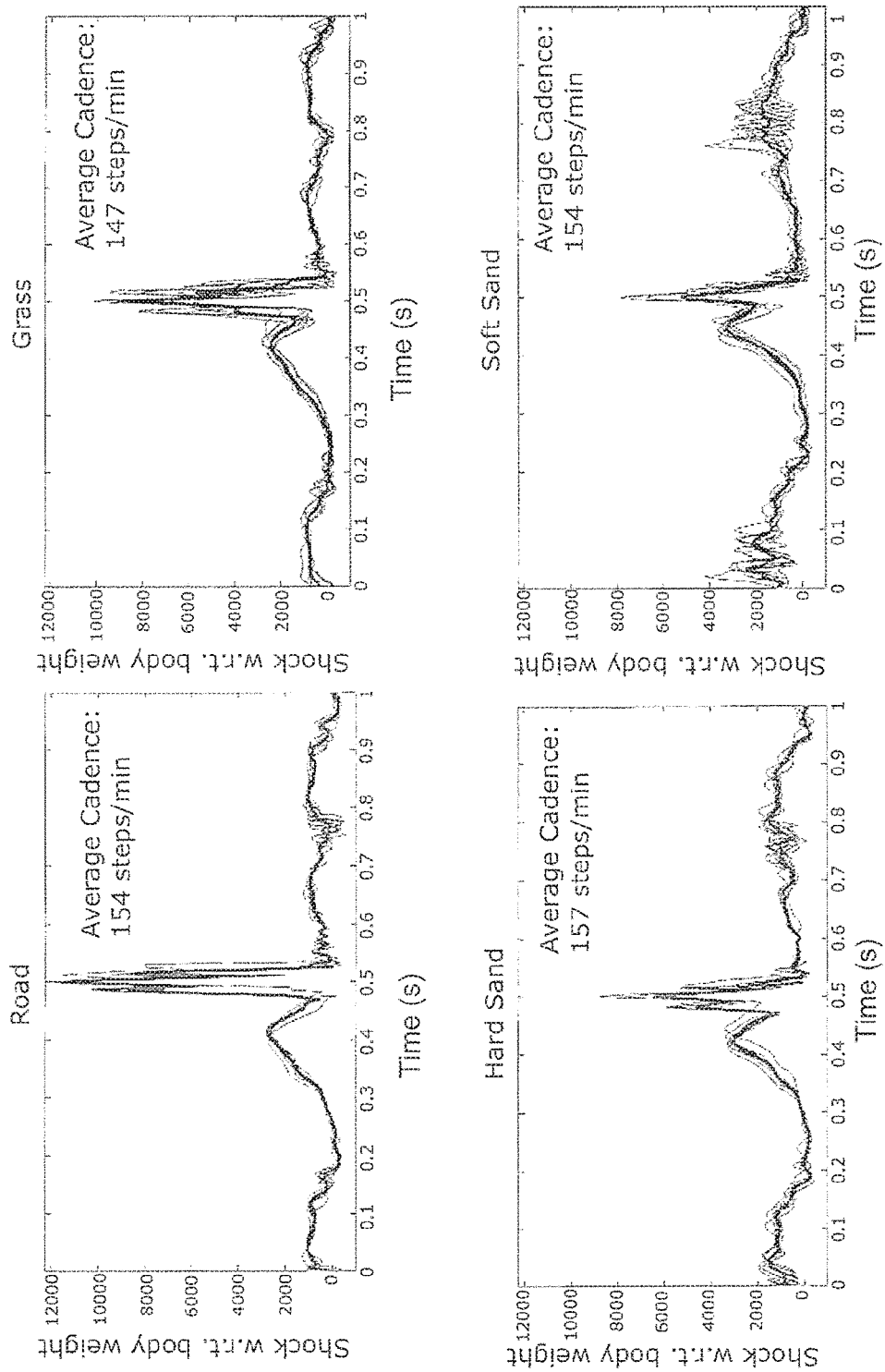
FIG. 7F shows graphs plotting an overlay of resultant acceleration magnitude data, normalized with respect to body weight, against time, the data corresponding to that from FIGS. 7A-7D for the 4 different terrains.

FIG. 7F show an overlay of 11 step s/footstrikes for each terrain from the data in FIGS. 7A-7D. It can be seen that the shock signature of each different step is in fact a recurring pattern dependent on the type of terrain. The thicker dark line represents the average shock signature.

Example Algorithm for Determining Cadence and Session Load Stimulus

Figure 8:
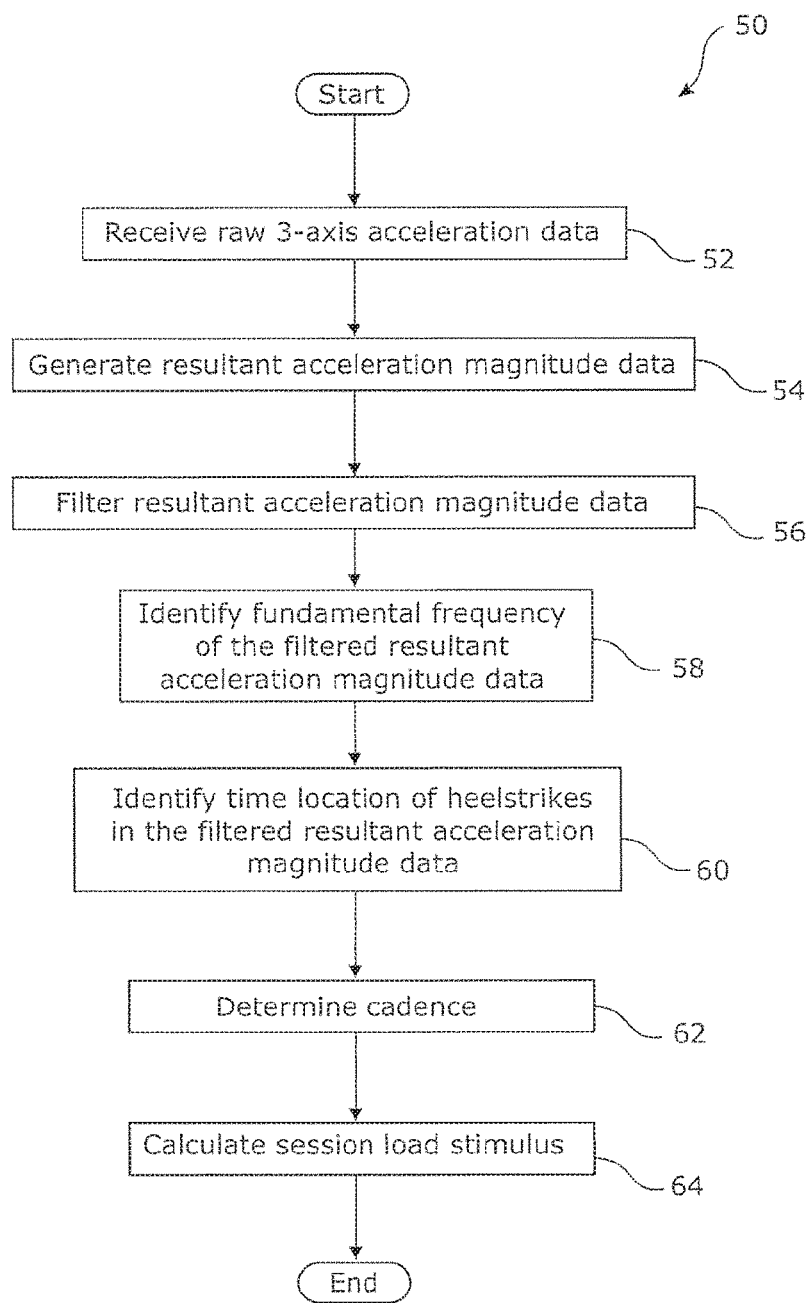
FIG. 8 shows a flow diagram of an example algorithm for data processing of received tibial shockwave data in accordance with an embodiment of the invention.

By way of example, an algorithm for determining cadence and session load stimulus from sensed tibial shockwave data recorded for a runner over an activity session will be described with reference to FIG. 8. In this example, the algorithm 50 executes once the full activity session data is available, i.e. post-processing, but it will be appreciated that the algorithm may be begin executed concurrently with the generation of the sensed tibial shockwave data once enough representative data is available to generate reliable results in alternative configurations. As described earlier, the data processing performed by the algorithm may be executed onboard the motion sensor 14 itself, or the algorithm may be operating on a remote computing device 32 communicatively coupled or connected (e.g. wireless or hardwired) to the motion sensor 14 which receives and processes the sensed data from the motion sensor.

The algorithm 50 starts by receiving the tibial shockwave data from the motion sensor 14 attached to the runner's lower limb at step 52. In this example, the tibial shockwave data is in the form of raw 3-axis acceleration data sensed by the 3-axis accelerometer of the motion sensor 14. The raw 3-axis acceleration data is typically provided in digital form as a time-series, sampled from the analogue acceleration signals. However, in alternative configurations the analogue signal may be received and digitised by the algorithm. An acceleration magnitude vector is then calculated for the received 3-axis acceleration data to generate resultant acceleration magnitude data at step 54. This resultant acceleration magnitude data is calculated using equation (1) above, i.e. by square rooting the sum of the squares of all 3 acceleration measures at each time-sample.

The resultant acceleration magnitude data is then filtered to remove noise at step 56. In this example, the data is subjected to a bandpass filter that is configured to filter out excessively high frequency noise such as skin movement, and also very low frequency movement that is much below the frequency of a runner. The filtered resultant acceleration magnitude data is then processed to identify the fundamental frequency at step 58. In this example, the fundamental frequency is identified using a fast fourier transform and wavelet techniques. The value and power of the identified fundamental frequency is then reviewed against threshold ranges to determine whether it is within an appropriate range for running data.

As shown at step 60, the filtered acceleration magnitude data is then filtered further, this time at double the fundamental frequency (the nyquist frequency) to determine the approximate time location of the heelstrikes in the data. A running window is then applied in step 60 to the data to find the exact time location of the heelstrikes by searching near the previously determined approximate location of the individual heelstrikes.

Cadence associated with the activity session is then determined by analysing the determined time locations of the individual heelstrikes at step 62. In this example, data indicative of the cadence is generated by calculating the average time between each identified heelstrike.

The peak shock associated with each discrete footstrike in the data, i.e. the magnitude of the resultant acceleration magnitude data at the identified heelstrike locations, is then extracted. This peak shock data is then input into an algorithm that calculates a session load stimulus (eDLS), an example of which is described below in relation to the second embodiment and equation (2).

2. First Embodiment—Real-Time Running Gait Feedback System

The shape and form of an individual's tibial 'shock signature' allows the quantification of metrics such as runner deviation, i.e. the deviation from their normal signature shock. This means that changes in the runner's gait can be identified, and with the right processing tools we can quantify these differences and infer smart conjectures about how the runner should alter their gait to return to their best form. Other metrics such as cadence can also be measured.

The use of tri-axial accelerometry to measure individual and resultant tibial shock allows the analysis of a subject's foot strike in three dimensions, which can be used to assist in changing the subject's running technique if it means they will receive less tibial shock. The sensors ability to reproduce body movement in 3D space can be used to visualize a person's technique in a virtual simulation program (e.g. OpenSim, Stanford Calif.).

Figure 9:
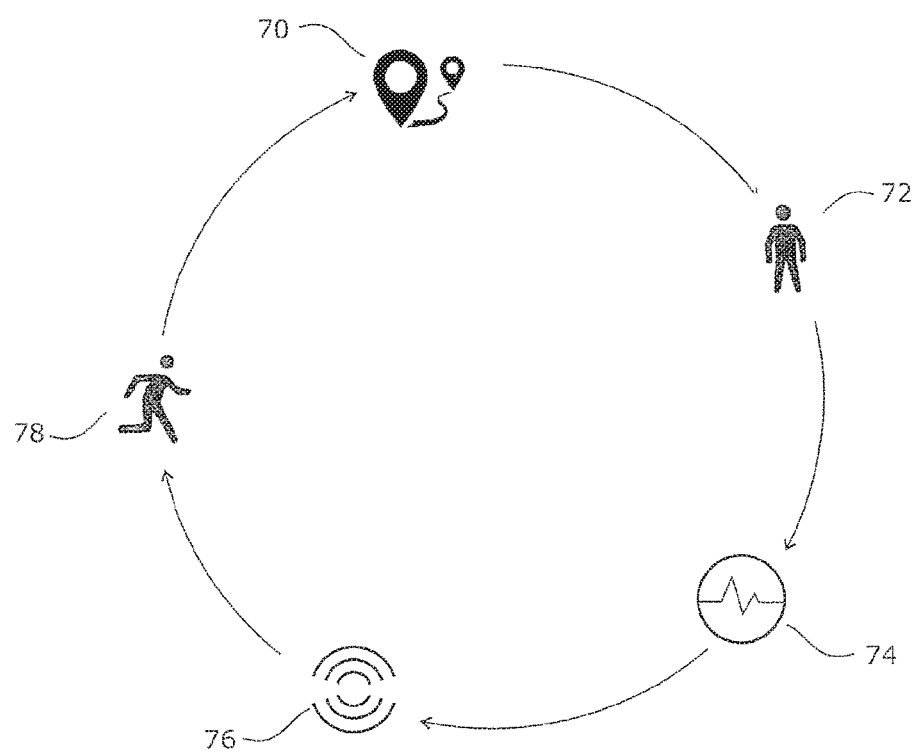
FIG. 9 shows a flow diagram of a real-time running gait feedback system using data sensed by the motion sensor of the lower limb loading assessment system.
Figure 10A:
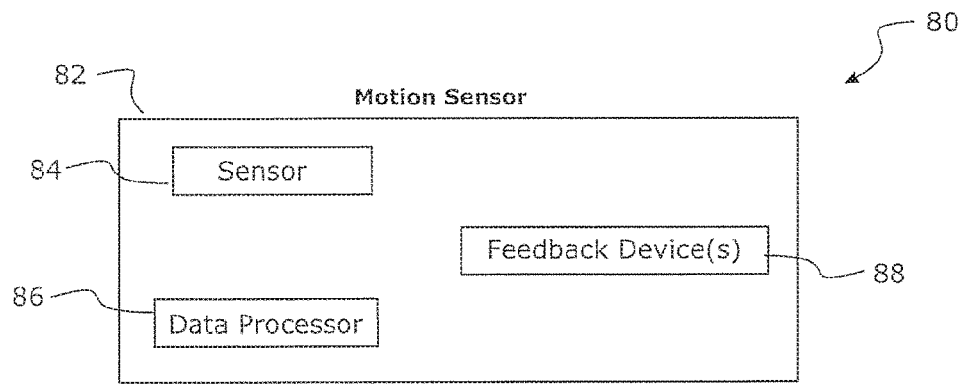
FIGS. 10A-10C show schematic diagrams of the hardware components of the real-time running gait feedback system in accordance with various configurations of the invention.
Figure 10B:
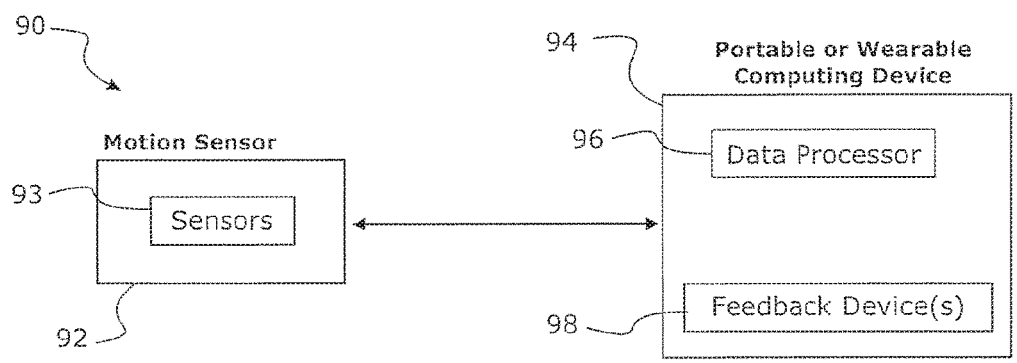
Figure 10C:
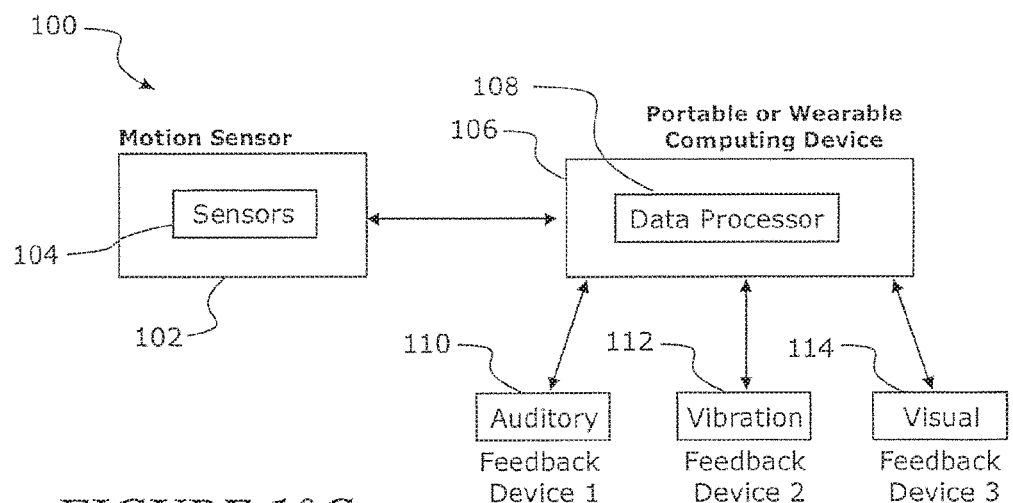

Referring to FIGS. 9-10C, an implementation of the lower limb loading assessment system as a real-time running gait feedback system will be described. Referring firstly to the feedback loop in FIG. 9, the feedback system is intended to provide a runner with real-time feedback about their running style, and whether it has deteriorated, during an activity session, such as running a route. In particular, the running may be running a route as shown at 70. During that run, the runner's form, technique or style may change, e.g. due to fatigue, injury, change in speed, terrain or some other reason, as shown at 72. The change in the runner's form results in a changed shock signature sensed by the motion sensor 14 attached to their lower limb as indicated at 74. This change in shock signature is detected by the feedback system, and if significant triggers the initiation of a feedback alert to the user.

The feedback system may be configured to trigger a feedback alert based on one or more selected changes in the shock signature relative to the user's normal signature. In one configuration, the peak shock associated with each footstrike is compared with a threshold, and an alert is generated if the peak shock exceeds the threshold. In another configuration, a moving average peak shock is calculated and continuously or periodically compared to a threshold, and an alert is generated if the average peak shock exceeds the threshold. In another configuration, the footstrike pattern associated with each footstrike is compared with the user's stored 'normal' shock signature, either in three dimensions with respect to each acceleration axis or on the basis of the profile of the resultant acceleration magnitude data of each footstrike, and an alert is generated if the footstrike pattern deviates beyond a predetermined range relative to the normal shock signature. It will be appreciated that one or more of the previous comparisons may be carried out in data processing concurrently to decide whether to generate an alert. Additionally, a range of different types of alerts may be provided depending on the change in the running style, or the magnitude of the alert may varying according to the magnitude of the deviation from the user's normal running style.

If an alert is triggered, an alert control signal is generated, and this causes tactile, audio and/or visual feedback to be provided to the runner to alert them to the deterioration in the running style at 76. In response to the feedback, the runner adjusts their form at 78 until the alert ceases to thereby return their running style to the desired form for injury mitigation.

The hardware configuration of the real-time running gait feedback system may be provided in various configurations, some embodiments of which will be described with reference to FIGS. 10A-10C. The configurations correspond or are based around the system previously described with reference to FIGS. 1-3. The example configurations will be described with reference to the main components of the system, namely the motion sensor comprising the 3-axis accelerometer for sensing the tibial shockwave data, the data processing, and feedback device(s). The configurations show that these components may be combined in a single device or alternatively dispersed amongst two or more separate but communicatively coupled devices.

Referring to a first configuration 80 in FIG. 10A, the feedback system may be embodied in a single device, namely the motion sensor 82 worn by the user. In particular, the motion sensor 82 comprises the accelerometer sensor 84, data processor 86, and the feedback device or devices 88. For example, the data processor generates an alert control signal when processing the sensor data when detecting a deviation in the user's tibial shockwave data, and the alert control signal is configured to operate one or more feedback devices onboard the motion sensor. The feedback device(s) may comprise a tactile vibration device or element, and/or an auditory component for generating an audible alert. As the motion sensor 82 is mounted to the user's lower limb, they will feel the vibration at their lower limb or the audible alert emanating from the sensor on their lower limb.

Referring to a second configuration 90 in FIG. 10B, the feedback system is implemented by a motion sensor 92 worn on the user's lower limb as previously described and which comprises at least the 3-axis accelerometer 93, and which is communicatively coupled, e.g. over a wireless data connection, to a portable or wearable computing device 94 held, worn or otherwise attached or carried by the user. By way of example, the computing device 94 may be a smart phone or smart watch, and the computing device comprises the data processor 96 and feedback device(s) 98. In particular, the raw acceleration data is transmitted from the motion sensor onboard the user's lower limb to their smart phone or smart watch which they are carrying, holding or otherwise wearing. The received tibial shockwave data is processed, and the relevant alert control signals are triggered when the runner's style deviates as previously described. By way of example, the data processor 96 is implemented by the processor of the smart phone or smart watch, and the feedback device(s) 98 may comprise the vibration or audio output components or hardware of the smart phone or smart watch.

Referring to a third configuration 100 in FIG. 10C, the motion sensor, data processor and feedback device(s) may be separate components worn or carried by the user that are all communicatively coupled over one or more data links, whether wireless or hardwired. For example, the motion sensor 102 with accelerometer 104 is worn on the user's lower limb, and transmits the sensed tibial shockwave data to the data processor 108 onboard a portable or wearable computing device 106, e.g. a smart phone or smart watch. The computing device 106 then operates or controls one or more feedback devices worn or carried by the user via alert control signals. The feedback devices may comprise any one or more of auditory feedback devices 110, such as buzzers or similar, tactile feedback devices 112, such as vibrator devices or similar, and/or visual feedback devices 114, such as LED lights or display devices.

3. Second Embodiment—A Cumulative Load Monitoring System

Figure 11:
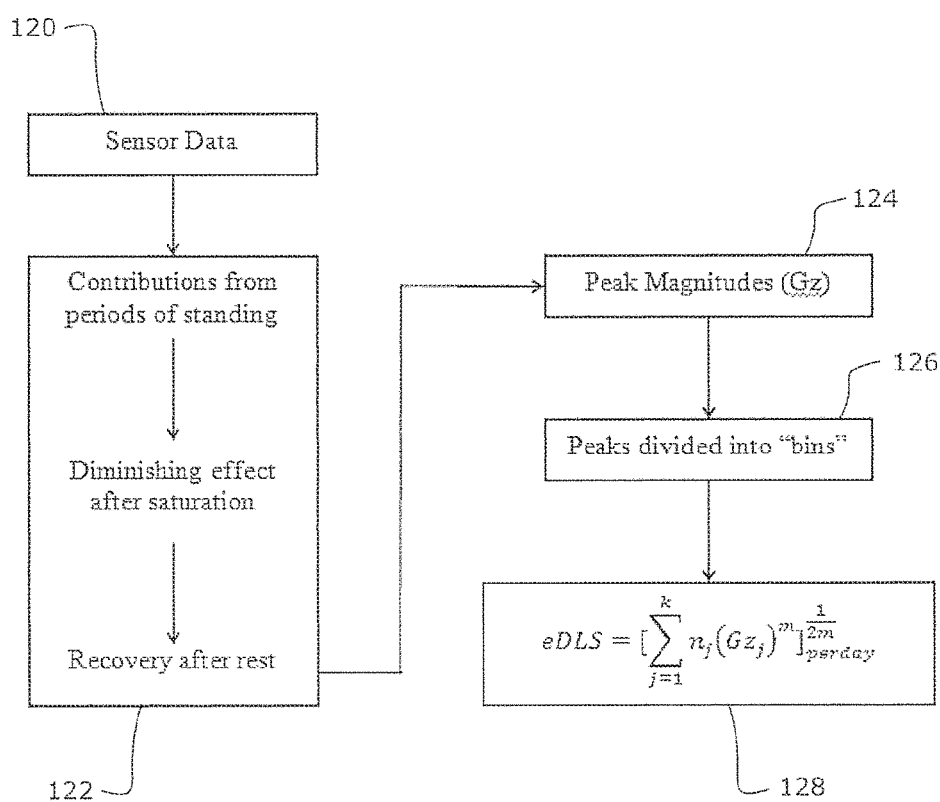
FIG. 11 is a flow diagram of a cumulative loading monitoring system in accordance with an embodiment of the invention.

Referring to FIG. 11, a cumulative load monitoring system embodiment of the lower limb loading assessment system will be described. The system employs the general hardware system and components discussed with reference to FIGS. 1-3. The cumulative load monitoring system is configured to generate a Daily Load Stimulus (DLS) metric in response to the tibial shockwave data sensed by the motion sensor when the user is engaged in activity sessions throughout the day.

Musculoskeletal tissue, such as bone, adapts to its mechanical environment by sensing the local tissue deformations (strains). Daily Load Stimulus (DLS) uses tissue stress as a key indicator for load. The DLS is important because it is a method that quantifies the daily stress histories of bone in terms of daily cyclic stress magnitudes and the number of daily loading cycles (i.e. total loading exposure). This information aids in defining the amount of stresses and loads imposed on the bones within the leg over longer time periods (e.g. days) rather than transient ones (e.g. one foot strike).

The sensed data from the motion sensor 14 can also be used to quantify and monitor the DLS of an individual when they are engaged in activity sessions, e.g. running. In particular, in this cumulative load monitoring system the subject can be provided with a motion sensor 14 that they wear when engaged in physical activity sessions and which is configured to continuously or periodically transmit sensed tibial shock data to the computing device 32 or a server for processing and monitoring. As previously described, the motion sensor 14 may periodically or continuously transmit the sensed data to any computing device 32 in communication range, such as a smart phone or smart watch carried or worn by the user over Bluetooth or any other wireless communication medium, or alternatively may be provided with a communication module that can communicate over a cellular connection, WiFi, or any other direct wireless data communication medium to the remote computing device 32 or server. Alternatively, the motion sensor 14 may store the data in onboard memory 27 for later download to a computing device when in range or otherwise operatively connected, e.g. by cable.

The cumulative load monitoring system is able to quantify an individual's daily load stimulus (DLS). The accumulative load monitoring system in this embodiment accounts for variables such as saturation and recovery of osteogenic potential with cyclical loading and standing.

Referring to FIG. 11, the process 100 of the accumulative load monitoring system is shown. The final equation:

$$eDLS = \left[ \sum_{j=1}^{k} n_j (Gz_j)^m \right]^{\frac{1}{2m}}_{per day} \quad (2)$$

is the estimated daily load stimulus (DLS) for the individual, where:
Gz=the peak magnitude of the force derived from F=m·a
j=number of loading conditions
m=weighting factor (e.g. 4)
k=number of different loading conditions Firstly, sensor data 120 is transmitted wirelessly from a motion sensor 14 worn by the user, as described previously, to a reciprocating receiver, such as a computing device 32. The receiver may be, but is not limited to, a smart phone, smart watch, or any other portable computing device 32 having a communication module such as Bluetooth 4.0 or similar. The sensor data 120 comprises linear accelerations in 3 axes, but may also include angular rates in 3 axes and magnetic field strength in 3 axes, if gyroscope 19 and/or magnetometer 20 sensors are also provided in the motion sensor 14 in order to get more information around sensor orientation.

Once the sensor data 120 is received at the computing device, the data is processed by algorithms that calculate the daily load stimulus (DLS) for the individual. The process that the algorithm runs through is as follows:

a. The magnitude of the acceleration vector is calculated by: $\bar{a} = \sqrt{a_x^2 + a_y^2 + a_z^2}$ b. The magnitude time series data (resultant acceleration magnitude data) is then run through an algorithm that detects and quantifies the peaks present, i.e. peak shock data (similar to that detected in the example algorithm 50 described previously). The peaks are directly related to the impact phase of a running stride. Each runner has a stored tibial 'shock signature' that is used in the process to detect future tibial shock impacts. The algorithm does the detection by using cross-correlation. Using cross-correlation, and other time series analysis techniques, such as Fourier Transforms, and Power Spectral Densities (PSD), the algorithm is able to quantify whether the athlete is running, walking, or resting, and this is shown generally at step 122.

c. Once all of these activities have been quantified and individual tibial shock peaks identified 124, the peak accelerations are recorded and stored 126 for each impact phase in both running and walking.

d. The stored data is continually updated and processed calculating the cumulative load stimulus 128, taking into account the different effects of running, walking, standing, and recovery.

e. Bone Stimulus Saturation is taken into account by:
   i. Once saturation has been reached the peak tibial accelerations are multiplied by the hyperbolic function $1/(1+N)$ where N is the number of cyclic loads after saturation. This models the cumulative load after saturation is reached. Saturation was assumed after 5 min of continuous running, 10 min of continuous walking or equivalent. This threshold however is context dependent and may vary based on factors such as age and sex.
   ii. Recovery is then modeled by the equation $100(1-e^{-t/\tau})$ where t is time in hours between bouts and $\tau$ is a time constant (2 hours). Each successive bout of walking or running that occurred after saturation was then multiplied by the recovery equation.
   iii. Once the data has been segmented into their respective activities (i.e. running, walking, rest etc.), the magnitudes of the tibial accelerations are stored in a buffer that is continually processed by eDLS equation.
   iv. Using the eDLS equation we can quantify Bone Stimulus Saturation and Tibial Shock over longer time periods rather than smaller time transients.

The calculated estimate daily load stimulus can be utilised in various applications, some examples of which are set out below.

Footwear Application

The monitored eDLS generated by the cumulative load monitoring system may be compared to a threshold level for the individual for the purpose of identifying when the individual's footwear may be deteriorating or no longer providing adequate attenuation of the tibial shockwaves. If the eDLS exceeds the threshold level, the individual may be alerted or notified by the system that their running shoes no longer reduce tibial shock to adequate levels.

Activity Session Load Stimulus Application

The above algorithm for estimating daily load stimulus is explained in the context of combining tibial shockwave data over a plurality or multiple activity sessions in a day. However, it will be appreciated that the algorithm may also be applied to a single set of tibial shockwave data from a single activity session and in this context the calculated eDLS represents a session load stimulus (SLS).

4. Third Embodiment—Shoe-Fitting Feedback System

With reference to FIGS. 12A-15, a shoe-fitting feedback system embodiment of the lower limb loading assessment system will be described. The shoe-fitting system employs the same hardware configuration and components as described with reference to FIGS. 1-3 and is configured to quantify the different levels of tibial shock that arise from running with different respective pairs of shoes. This information is used to provide a customer with a pair of shoes that suits their own personal gait. The shoe-fitting system uses a tibial shock metric, such as a tibial shock score, to identify a pair of shoes that reduce loading to the knee of a subject person. Optionally, the shoe-fitting system may also comprise a treadmill or similar exercise platform, provided with forward and backward facing cameras capturing the subject's running style on the treadmill.

Different shoes exhibit varying levels of stiffness and cushioning, leading to differences in the attenuation of shock into the lower limb during running. Therefore the type of shoe that a person wears when they run will affect the magnitude as well as distribution of the travelling shockwave, which in turn will change the force profile transmitted to the leg and hence chance of injury for that individual.

The typical shoe-fitting process using the shoe-fitting feedback system will now be described in further detail, by way of example only. A customer comes into a store, has their feet measured, and tries on a pair of shoes suggested by the shop assistant. The motion sensor 14 is then strapped on to one of the customer's lower legs, for example at a position just above the lateral malleolus of the fibula on the subject's ankle. The motion sensor 14 is then switched on using the user interface 23 provided on the motion sensor 14. The customer is then asked to get on the treadmill, and the shop assistant speeds the treadmill up to a constant speed ensuring the customer is running at comfortable pace.

During this activity session, the motion sensor 14 is configured to measure each discrete tibial shockwave experienced by the customer's monitored lower leg as they run and generates representative tibial shockwave data. Referring to FIG. 4B, an example of the accelerations measured in the three sensor axes 20 for a single foot-strike on the treadmill is shown. The tibial shockwave data transmitted to the computing device 32 represents a series of discrete tibial shockwaves, like the data shown in FIG. 4A, for each foot-strike as the customer runs for the activity session, which may be monitored for a predetermined time period, say 20-30 seconds for example, although this may be longer or shorter depending on the circumstances.

In this embodiment, the computing device 32 is configured to receive the raw three-axis acceleration data, and is configured to calculate a time-series of the resultant acceleration magnitude data representing the tibial shockwave data from the motion sensor. Alternatively, the resultant acceleration magnitude data may be calculated onboard the motion sensor and transmitted to the receiver 28 for the computing device 32.

At the end of each activity session, the computing device 32 is configured to determine the peak resultant acceleration magnitude for each discrete tibial shockwave in the series of foot strikes from the activity session. The computing device is then configured to calculate the average peak resultant acceleration magnitude of the foot strikes for the activity session, and this is output or stored directly as a tibial shock score for the activity session, or alternatively the average peak resultant acceleration magnitude is converted into a normalized value within a predetermined tibial shock score scale and output or stored as the tibial shock score for the activity session. The average peak resultant acceleration magnitude may also be normalised with respect to the person's body weight, speed, or effective body mass (taking into account the degree of knee flexion).

In one embodiment, the computing device 32 may receive user input identification data identifying the type of footwear being worn by the customer during the activity session. The computing device 32 is then able to link the tibial shockwave data and/or tibial shock score from the activity session to the particular footwear being worn.

The above process is then repeated for the customer for a plurality of different types of shoes and the tibial shockwave data for each activity session or shoe trialled is sensed, processed and stored as above.

Once all shoes have been trialled through a respective activity session on the treadmill, the computing device 32 is configured to undertake a comparative analysis of the data from each activity session and generate assessment data to assist the shop assistant in recommending or selecting the footwear that is likely to result in reduced lower limb impact for the customer.

Figure 12A:
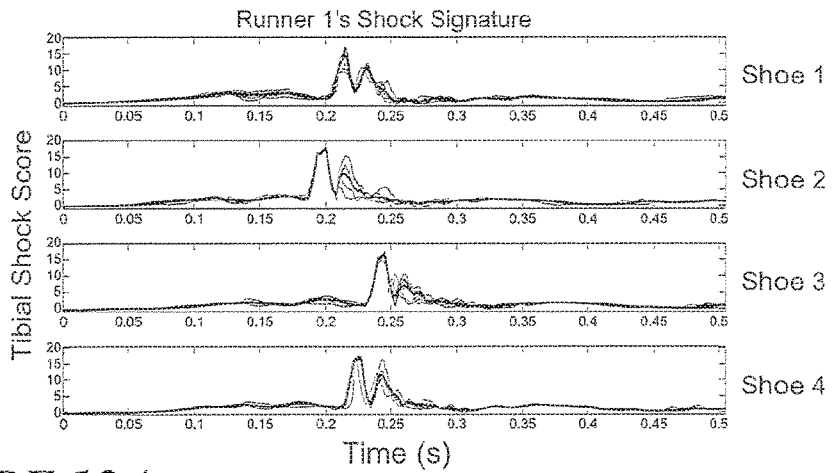
FIGS. 12A-12C show graphs plotting an overlay of normalized resultant acceleration magnitude data, representing the discrete tibial shockwaves sensed over 4 separate activity sessions for each of three different runners, the runners wearing different footwear in each activity session, the data gathered for a shoe-fitting feedback system in accordance with an embodiment of the invention.
Figure 12B:
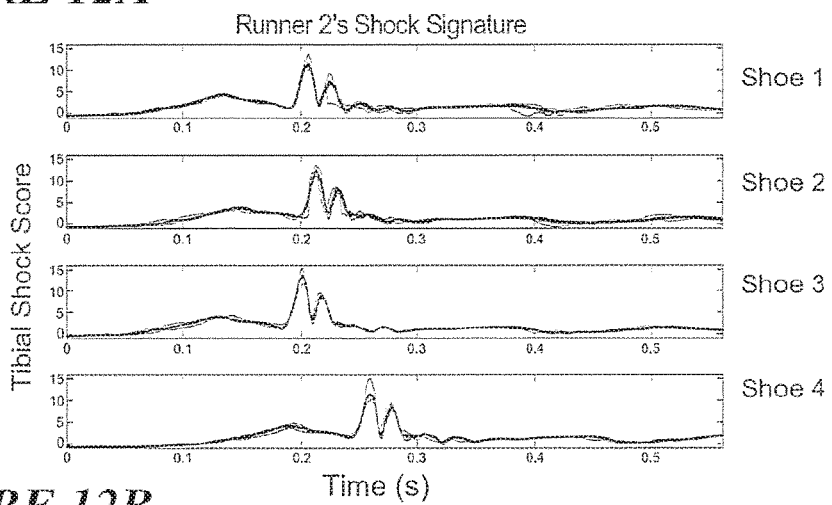
Figure 12C:
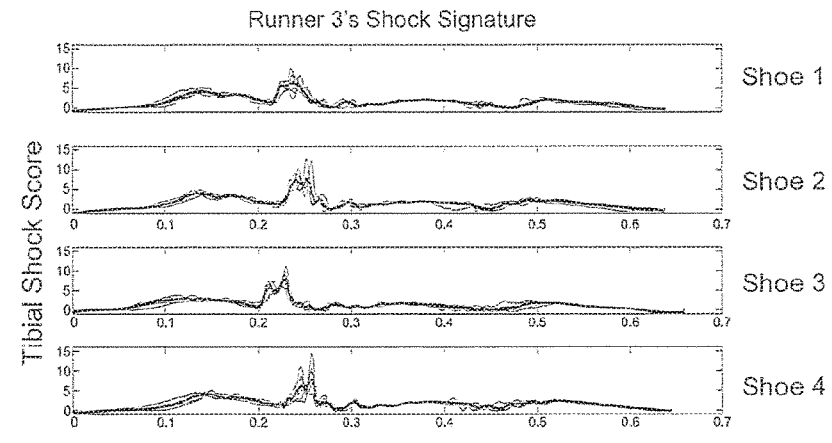
Figures 13A, 13B, 13C:
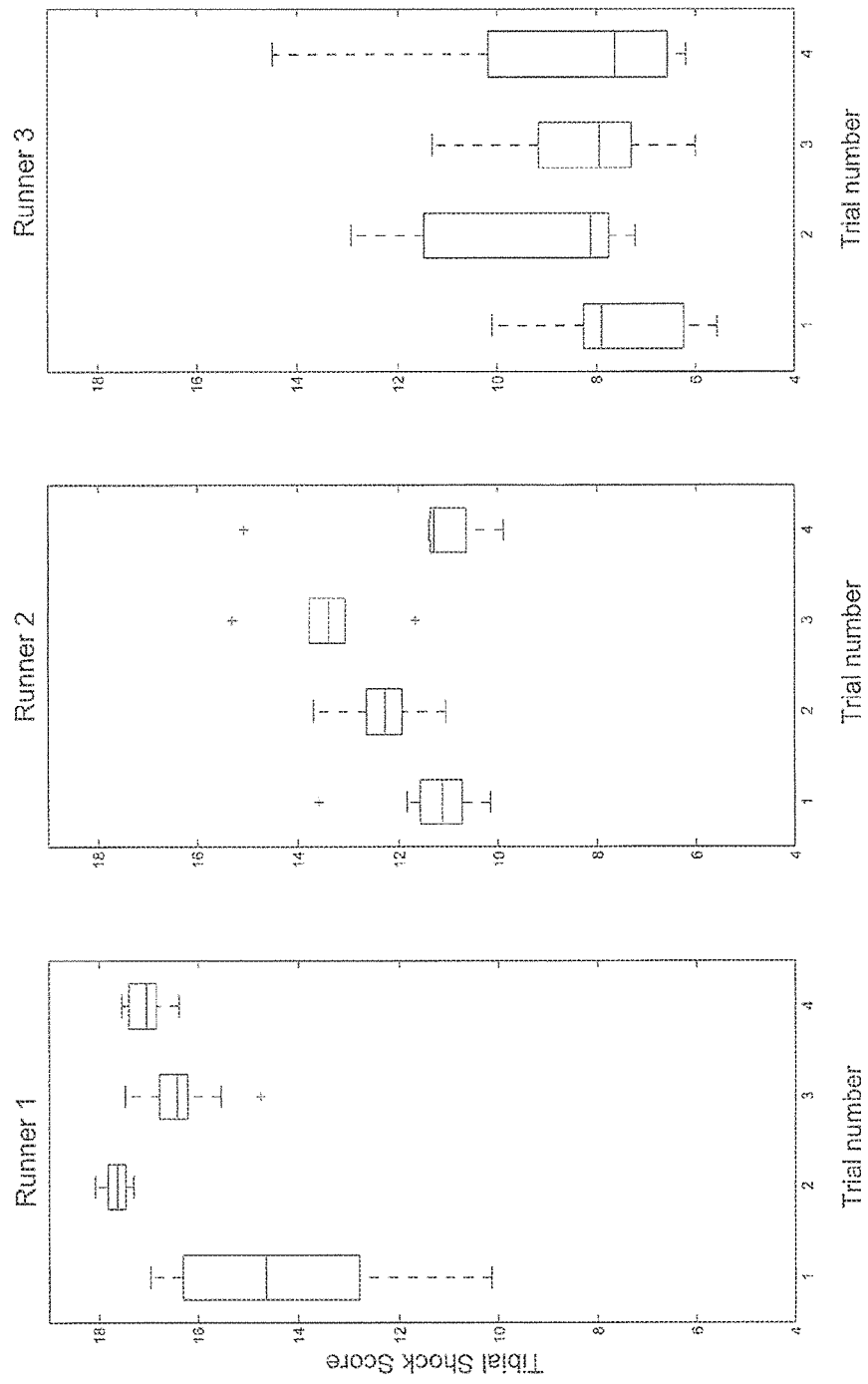
FIGS. 13A-13C show respective box-and-whisker plots of the normalized peak resultant acceleration magnitude data shown in FIGS. 11A-11C.
Figure 14:
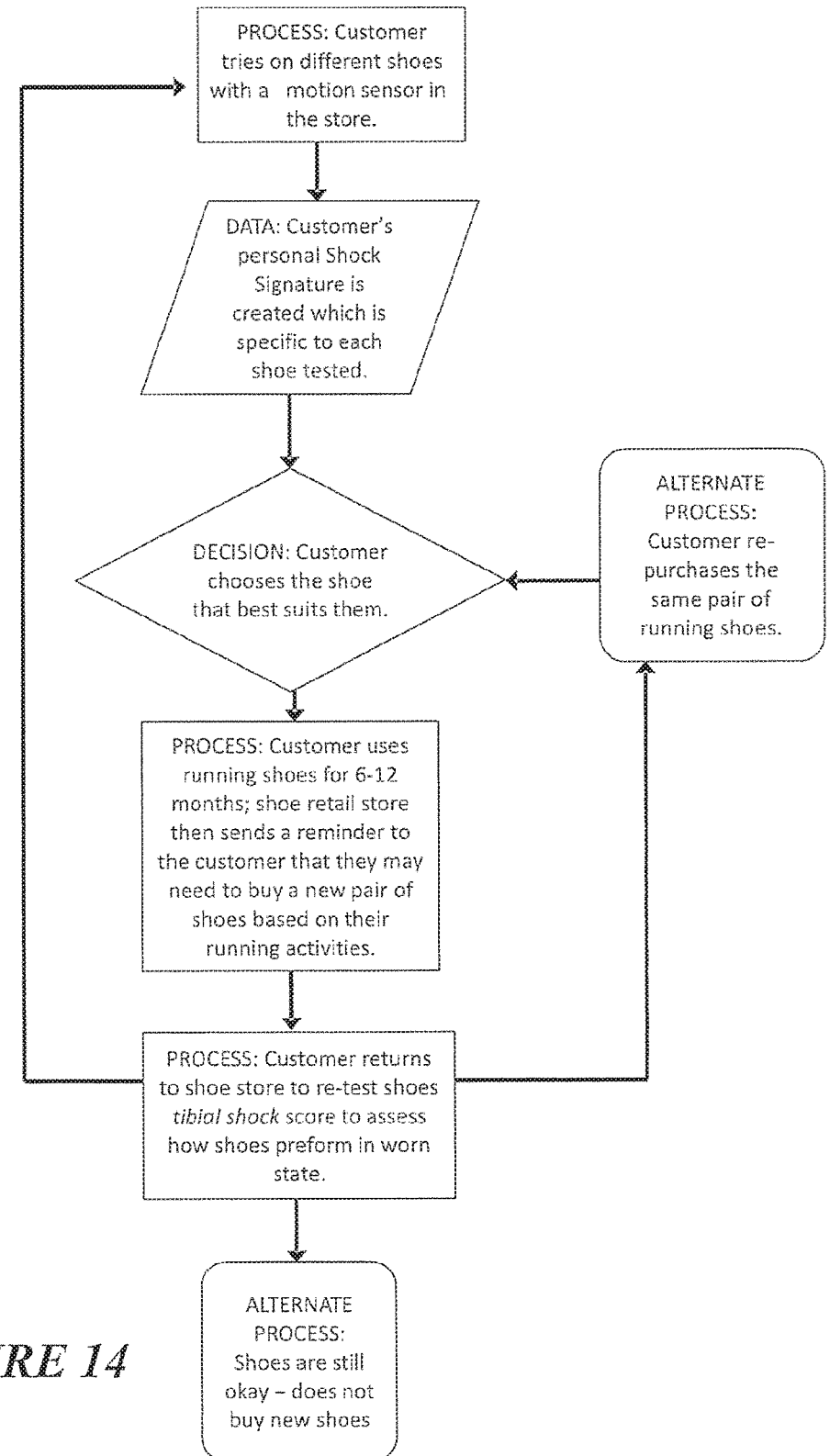
FIG. 14 is a flow diagram showing a follow-up assessment process after an initial shoe-fitting process carried in accordance with the shoe-fitting feedback system.
Figure 15:
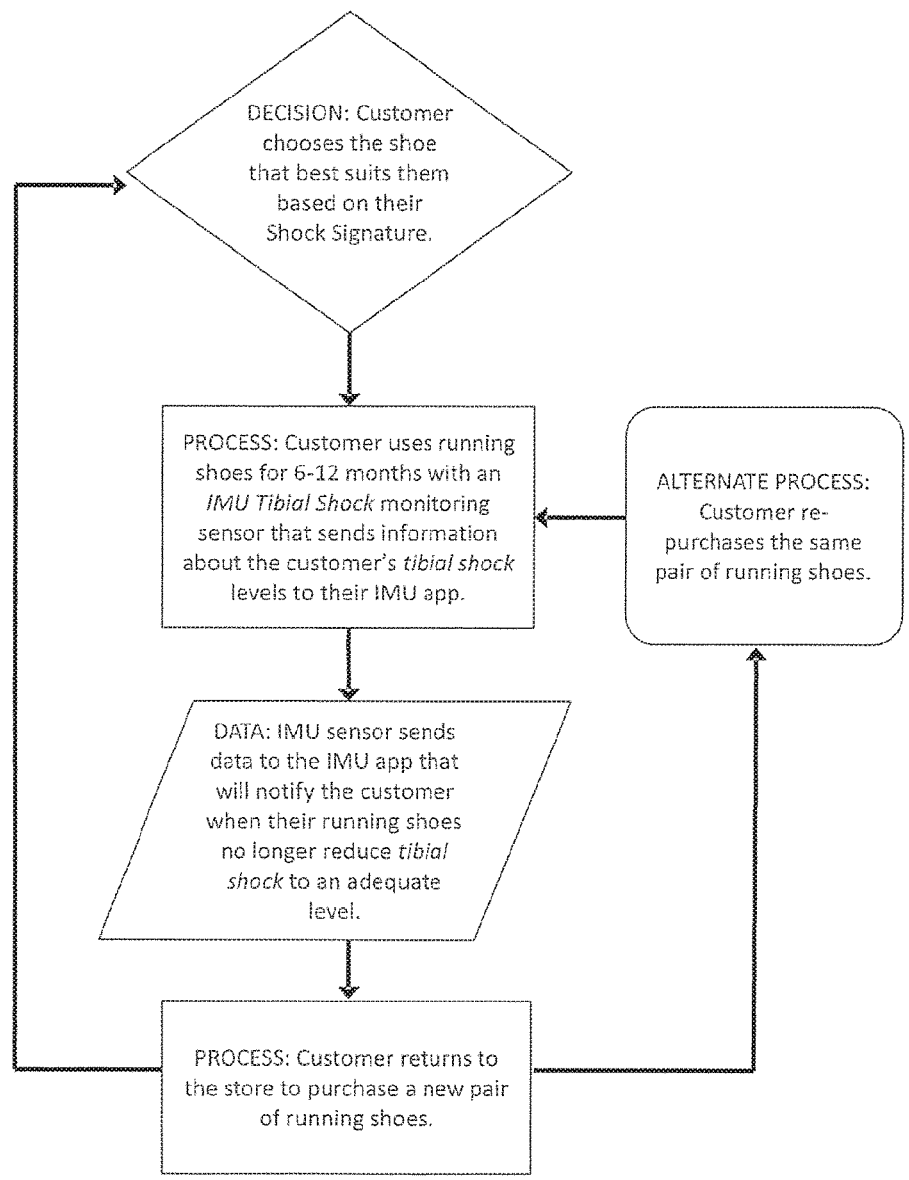
FIG. 15 is a flow diagram showing a long-term feedback monitoring process associated with the shoe-fitting feedback system.

By way of example, FIGS. 12A-12C show graphs of results of the resultant acceleration magnitude data sensed over 4 separate activity sessions, for three different runners. In each separate activity session, the runner wore a different type of running shoe (shoes 1-4). In the graphs, the discrete tibial shockwaves for each foot strike in the monitored period are overlaid upon each other rather than serially presented in the timeline. FIGS. 13A-13C depict the corresponding box-and-whisker plots of the data depicted in FIGS. 12A-12C respectively.

The computing device 32 may generate and display assessment data based on the collective data from the activity sessions. The computing device 32 may be configured to display graphs as above in FIGS. 12A-12C, or corresponding data tables for example. The computing device 32 may also be configured to generate assessment data based on comparison of the data from the activity sessions. In one form, the computing device 32 may output or display data indicative of the activity session and/or shoe having the lowest associated tibial shock score and therefore is the optimal shoe for the customer and their running style. Alternatively, the computing device 32 may output or display the tibial shock score associated with each shoe trialled for the shop assistant and customer to review and consider.

Reverting to FIGS. 13A-13C, it can be seen that the 3 different runners each had unique tibial shockwave data when trialling the 4 different shoes, and the same type of shoe is not necessarily optimal for each runner.

In an embodiment, the customer's tibial shockwave data for each shoe may be stored in the computing device 32 or an associated database or storage medium for future use. For example, referring to the flow chart of FIG. 14, the customer may be sent a reminder to return to the shoe store after 6-12 months of using their shoes, to re-assess their tibial shock score when the shoes are in a worn-state. Depending on the results relative to the original tibial shock score in a new state, a new pair of shoes may be recommended or the shoes may be deemed to still be in adequate condition for further use. In another example, referring to FIG. 15, the customer may be provided with a motion sensor for wearing while running over a time period, say 6-12 months. The motion sensor sends the tibial shockwave data to the computing device during each running session and is configured to assess the tibial shockwave data to determine when the customer's running shoes no longer reduce tibial shock to an adequate level. This analysis may be based on comparing the tibial shockwave data or parameters extracted from the tibial shockwave data, such as peak shock, average peak shock, and/or shock signature, to predetermined thresholds or threshold ranges.

5. General

Furthermore, embodiments may be implemented by hardware, software, firmware, middleware, microcode, or any combination thereof. When implemented in software, firmware, middleware or microcode, the program code or code segments to perform the necessary tasks may be stored in a machine-readable medium such as a storage medium or other storage(s). A processor may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

In the foregoing, a storage medium may represent one or more devices for storing data, including read-only memory (ROM), random access memory (RAM), magnetic disk storage mediums, optical storage mediums, flash memory devices and/or other machine readable mediums for storing information. The terms "machine readable medium" and "computer readable medium" include, but are not limited to portable or fixed storage devices, optical storage devices, and/or various other mediums capable of storing, containing or carrying instruction(s) and/or data.

The various illustrative logical blocks, modules, circuits, elements, and/or components described in connection with the examples disclosed herein may be implemented or performed with a general purpose processor, a digital signal processor (DSP), an application specific integrated circuit (ASIC), a field programmable gate array (FPGA) or other programmable logic component, discrete gate or transistor logic, discrete hardware components, or any combination thereof designed to perform the functions described herein. A general purpose processor may be a microprocessor, but in the alternative, the processor may be any conventional processor, controller, microcontroller, circuit, and/or state machine. A processor may also be implemented as a combination of computing components, e.g., a combination of a DSP and a microprocessor, a number of microprocessors, one or more microprocessors in conjunction with a DSP core, or any other such configuration.

The methods or algorithms described in connection with the examples disclosed herein may be embodied directly in hardware, in a software module executable by a processor, or in a combination of both, in the form of processing unit, programming instructions, or other directions, and may be contained in a single device or distributed across multiple devices. A software module may reside in RAM memory, flash memory, ROM memory, EPROM memory, EEPROM memory, registers, hard disk, a removable disk, a CD-ROM, or any other form of storage medium known in the art. A storage medium may be coupled to the processor such that the processor can read information from, and write information to, the storage medium. In the alternative, the storage medium may be integral to the processor.

One or more of the components and functions illustrated the figures may be rearranged and/or combined into a single component or embodied in several components without departing from the invention. Additional elements or components may also be added without departing from the invention. Additionally, the features described herein may be implemented in software, hardware, as a business method, and/or combination thereof.

In its various aspects, the invention can be embodied in a computer-implemented process, a machine (such as an electronic device, or a general purpose computer or other device that provides a platform on which computer programs can be executed), processes performed by these machines, or an article of manufacture. Such articles can include a computer program product or digital information product in which a computer readable storage medium containing computer program instructions or computer readable data stored thereon, and processes and machines that create and use these articles of manufacture.

The foregoing description of the invention includes preferred forms thereof. Modifications may be made thereto without departing from the scope of the invention as defined by the accompanying claims.

The invention claimed is:

1. A lower limb loading assessment system comprising:
   at least one wearable motion sensor releasably securable to a subject's lower limb that is configured to sense the tibial shockwaves experienced by the lower limb as the subject performs a repetitive physical activity involving repetitive footstrikes of the lower limb with a surface, the wearable motion sensor comprising an accelerometer that is configured to sense acceleration data in at least three orthogonal axes and generate representative multi-axis acceleration data over a time period associated with the physical activity, the wearable motion sensor generating tibial shockwave data comprising the generated multi-axis acceleration data which represents a series of discrete tibial shockwaves from the discrete footstrikes; and
   a data processor that is configured to receive and convert the tibial shockwave data comprising the multi-axis acceleration data sensed by the wearable motion sensor into resultant acceleration magnitude data, and wherein the data processor is configured to process the resultant acceleration magnitude data to generate output feedback data comprising data to assist the subject to minimize future loading in their lower limbs.

2. The lower limb loading assessment system according to claim 1 wherein the data processor is further configured to extract or calculate one or more variables from the received tibial shockwave data or resultant acceleration magnitude data and compare the or each variable to a predetermined threshold or thresholds, and provide feedback data in the form of a real-time alert signal if one or more of the thresholds is exceeded by its associated variable.

3. The lower limb loading assessment system according to claim 2 wherein the data processor is configured to extract peak shock variables representing the peak resultant acceleration magnitude data associated with each discrete footstrike.

4. The lower limb loading assessment system according to claim 3 wherein the data processor is configured to generate a real-time alert signal if any peak shock variables exceed a predetermined threshold.

5. The lower limb loading assessment system according to claim 3 wherein the data processor is configured to calculate an average peak shock variable representing the average of the extracted peak shock variables, and wherein the data processor is configured to generate a real-time alert signal if the average peak shock variable exceeds a predetermined threshold.

6. The lower limb loading assessment system according to claim 2 wherein the data processor is configured to generate footstrike pattern variables representing the footstrike pattern associated with each footstrike as defined by the profile of the resultant acceleration magnitude data for a period associated with each discrete footstrike, and generate a real-time alert signal if any of the footstrike pattern variables exceed a predetermined footstrike pattern threshold.

7. The lower limb loading assessment system according to claim 2 wherein the data processor is configured to generate footstrike pattern variables representing the footstrike pattern associated with each footstrike as defined by the profile of the acceleration data in three axes for a period associated with each discrete footstrike, and generate a real-time alert signal if any of the footstrike pattern variables exceed a predetermined footstrike pattern threshold.

8. The lower limb loading assessment system according to claim 6 wherein the data processor is configured to generate the footstrike pattern variables based on tibial shockwave data for each discrete footstrike between heelstrike and toe-off time locations.

9. The lower limb loading assessment system according to claim 2 wherein the system further comprises one or more feedback devices mounted to or carried by the user that are triggered by in response to a generated real-time alert signal.

10. The lower limb loading assessment system according to claim 9 wherein the feedback devices comprise any one or more of the following: tactile feedback devices, audible feedback devices, and/or visual feedback devices.

11. The lower limb loading assessment system according to claim 1 wherein the data processor is configured to process the tibial shockwave data to generate feedback data in the form of data indicative of a session load stimulus.

12. The lower limb loading assessment system according to claim 1 wherein the data processor is configured to receive tibial shockwave data from a plurality of activity sessions of the subject from a single day, and generate feedback data in the form data indicative of a daily load stimulus.

13. The lower limb loading assessment system according to claim 1 wherein the data processor is configured to identify the time locations of the heelstrikes associated with each footstrike, and generate feedback data in the form of cadence representing the average time between heelstrikes.

14. The lower limb loading assessment system according to claim 1 wherein the data processor is configured to:
   receive tibial shockwave data from a plurality of separate activity sessions,
   convert the 3-axes acceleration data of the tibial shockwave data into resultant acceleration magnitude data,
   extract peak shock values representing the peak resultant acceleration magnitude associated with each discrete footstrike of the tibial shockwave data of each of the separate activity sessions, calculate the average peak resultant acceleration magnitude for each of the separate activity sessions based on the extracted peak shock values, and generate feedback data representing the calculated average peak resultant acceleration magnitude for each separate activity session.

15. The lower limb loading assessment system according to claim 14 wherein the subject is wearing a different type of footwear in each separate activity session, and the data processor is configured to receive or associate unique identification data relating to each different type of footwear used by the subject with the respective tibial shockwave data of each activity session, and the feedback data generated comprises data representing the calculated average peak resultant acceleration magnitude of each separate activity session linked with the unique identification data relating to the footwear used in the activity session.

16. The lower limb loading assessment system according to claim 14 wherein the data processor is further configured to compare the calculated average peak resultant acceleration magnitude associated with each activity session and generate further feedback data identifying the activity session having the lowest peak resultant acceleration magnitude.

17. The lower limb loading assessment system according to claim 1 wherein the accelerometer is a 3-axis accelerometer.

18. The lower limb loading assessment system according to claim 1 wherein the data processor is communicatively coupled to the wearable motion sensor over a data link.

19. The lower limb loading assessment system according to claim 1 wherein the data processor is onboard the wearable motion sensor.

20. The lower limb loading assessment system according to claim 1 wherein the wearable motion sensor is releasably securable to the subject's lower limb between the femoral epicondyle and medial malleolus.

21. The lower limb loading assessment system according to claim 1 wherein the wearable motion sensor is releasably securable to the subject's lower limb in the region of the lower $\frac{1}{3}^{rd}$ of the tibia.

22. The lower limb loading assessment system according to claim 1 wherein the wearable motion sensor is releasably securable to the subject's lower limb in the region of the medial part of the tibia.

23. The lower limb loading assessment system according to claim 22 wherein the wearable motion sensor is releasably securable to the subject's lower limb in the region adjacent and above the medial malleolus of the tibia.

24. The lower limb loading assessment system according to claim 1 wherein the wearable motion sensor is releasably securable to the subject's lower limb in the region adjacent and above the lateral malleolus of the tibia.

25. An electronic system for assessing the loading on a subject's lower limb as the subject performs a repetitive physical activity involving repetitive footstrikes of the lower limb with a surface, the system comprising a data processor configured to:

receive tibial shockwave data comprising sensed multi-axis acceleration data from at least one wearable motion sensor releasably secured to the subject's lower limb that comprises an accelerometer that is configured to sense and generate multi-axis acceleration data in at least three orthogonal axes, the sensed multi-axis acceleration data representing a series of discrete tibial shockwaves from the discrete footstrikes;

convert the tibial shockwave data comprising the multi-axis acceleration data into resultant acceleration magnitude data;

process the resultant acceleration magnitude data; and generate output feedback data comprising data to assist the subject to minimize future loading in their lower limbs.

26. The lower limb loading assessment system according to claim 7 wherein the data processor is configured to generate the footstrike pattern variables based on tibial shockwave data for each discrete footstrike between heelstrike and toe-off time locations.

27. The electronic system according to claim 25 wherein the data processor is further configured to extract or calculate one or more variables from the received tibial shockwave data or resultant acceleration magnitude data, compare the or each variable to a predetermined threshold or thresholds, and generate feedback data in the form of a real-time alert signal if one or more of the thresholds is exceeded by its associated variable.

28. The electronic system according to claim 27 wherein the data processor is further configured to extract peak shock variables representing the peak resultant acceleration magnitude data associated with each discrete footstrike.

29. The electronic system according to claim 28 wherein the data processor is further configured to generate a real-time alert signal is any peak shock variables exceed a predetermined threshold.

30. The electronic system according to claim 28 wherein the data processor is further configured to calculate an average peak shock variable representing the average of the extracted peak shock variables, and generate a real-time alert signal if the average peak shock variable exceeds a predetermined threshold.

31. The electronic system according to claim 27 wherein the data processor is further configured to generate footstrike pattern variables representing the footstrike pattern associated with each footstrike as defined by the profile of the resultant acceleration magnitude data for a period associated with each discrete footstrike, and generate a real-time alert signal if any of the footstrike pattern variables exceed a predetermined footstrike pattern threshold.

32. The electronic system according to claim 27 wherein the data processor is further configured to generate footstrike pattern variables representing the footstrike pattern associated with each footstrike as defined by the profile of the acceleration data in three axes for a period associated with each discrete footstrike, and generate a real-time alert signal if any of the footstrike pattern variables exceed a predetermined footstrike pattern threshold.

33. The electronic system according to claim 31 wherein the data processor is configured to generate the footstrike pattern variables based on tibial shockwave data for each discrete footstrike between heelstrike and toe-off time locations.

34. The electronic system according to claim 27 wherein the data processor is configured to trigger one or more feedback devices mounted to or carried by the user in response to a generated real-time alert signal.

35. The electronic system according to claim 34 wherein the feedback devices comprise any one or more of the following: tactile feedback devices, audible feedback devices, and/or visual feedback devices.

36. The electronic system according to claim 25 wherein the data processor is configured to process the tibial shockwave data to generate feedback data in the form of data indicative of a session load stimulus.

37. The electronic system according to claim 25 wherein the data processor is configured to receive tibial shockwave data from a plurality of activity sessions of the subject from a single day, and generate feedback data in the form data indicative of a daily load stimulus.

38. The electronic system according to claim 25 wherein the data processor is configured to identify the time locations of the heelstrikes associated with each footstrike, and generate feedback data in the form of cadence representing the average time between heelstrikes.

39. The electronic system according to claim 25 wherein the data processor is configured to:
receive the tibial shockwave data from a plurality of separate activity sessions, convert the 3-axes acceleration data of the tibial shockwave data into resultant acceleration magnitude data;
extract peak shock values representing the peak resultant acceleration magnitude associated with each discrete footstrike of the tibial shockwave data of each of the separate activity sessions;
calculate the average peak resultant acceleration magnitude for each of the separate activity sessions based on the extracted peak shock values; and
generate feedback data representing the calculated average peak resultant acceleration magnitude for each separate activity session.

40. The electronic system according to claim 39 wherein the subject is wearing a different type of footwear in each separate activity session, and the data processor is configured to receive or associate unique identification data relating to each different type of footwear used by the subject with the respective tibial shockwave data of each activity session, and the feedback data generated comprises data representing the calculated average peak resultant acceleration magnitude of each separate activity session linked with the unique identification data relating to the footwear used in the activity session.

41. The electronic system according to claim 39 wherein the data processor is further configured to compare the calculated average peak resultant acceleration magnitude associated with each activity session and generate further feedback data identifying the activity session having the lowest peak resultant acceleration magnitude.

42. The electronic system according to claim 25 wherein the accelerometer is a 3-axis accelerometer.

43. The electronic system according to claim 25 wherein the wearable motion sensor is releasably securable to the subject's lower limb between the femoral epicondyle and medial malleolus.

44. The electronic system according to claim 25 wherein the wearable motion sensor is releasably securable to the subject's lower limb in the region of the lower third of the tibia.

45. The electronic system according to claim 25 wherein the wearable motion sensor is releasably securable to the subject's lower limb in the region of the medial part of the tibia.

46. The electronic system according to claim 45 wherein the wearable motion sensor is releasably securable to the subject's lower limb in the region adjacent and above the medial malleolus of the tibia.

47. The electronic system according to claim 25 wherein the wearable motion sensor is releasably securable to the subject's lower limb in the region adjacent and above the lateral malleolus of the tibia.

48. The electronic system according to claim 32 wherein the data processor is configured to generate the footstrike pattern variables based on tibial shockwave data for each discrete footstrike between heelstrike and toe-off time locations.

* * * * *

UNITED STATES PATENT AND TRADEMARK OFFICE
CERTIFICATE OF CORRECTION

PATENT NO. : 10,405,780 B2
APPLICATION NO. : 15/128808
DATED : September 10, 2019
INVENTOR(S) : Finch et al.

Page 1 of 1

It is certified that error appears in the above-identified patent and that said Letters Patent is hereby corrected as shown below:

On the Title Page

Item (57), in "Abstract", in Column 2, Line 1, before "loading", insert --limb--

On page 2, in Column 1, item (56) under "Other Publications", Line 7, delete "PCT/ B2015/051206," and insert --PCT/IB2015/051206,-- therefor Signed and Sealed this
Seventh Day of April, 2020

Andrei Iancu
*Director of the United States Patent and Trademark Office*